United States Patent [19]
DeBernardis et al.

[11] Patent Number: 6,075,026
[45] Date of Patent: Jun. 13, 2000

[54] CERTAIN SUBSTITUTED 1-ARYL-3-PIPERAZIN-1'-YL PROPANONES

[75] Inventors: John Francis DeBernardis, Lindenhurst; Daniel Joseph Kerkman, Lake Villa; Raymond Paul Zinkowski, Northbrook, all of Ill.

[73] Assignee: Molecular Geriatrics, Corp., Vernon Hills, Ill.

[21] Appl. No.: 08/837,598

[22] Filed: Apr. 21, 1997

Related U.S. Application Data

[63] Continuation of application No. 08/341,481, Nov. 17, 1994, Pat. No. 5,658,909.

[51] Int. Cl.[7] ............... A61K 31/495; A61K 31/535; C07D 413/06
[52] U.S. Cl. ............ 514/255; 514/253; 514/252; 514/378; 514/322; 514/324; 514/326; 514/364; 514/231.8; 514/231.5; 544/367; 548/248
[58] Field of Search .................... 514/252, 253, 514/255, 378, 322, 324, 326, 364

[56] References Cited

U.S. PATENT DOCUMENTS 5,693,804  12/1997  DeBernardis et al. .................. 544/367

*Primary Examiner*—T J Criares
*Attorney, Agent, or Firm*—McDonnell, Boehnen, Hulbert & Berghoff

[57] ABSTRACT

Disclosed are compounds of formula I:

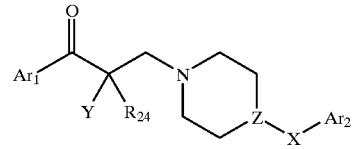

or the pharmaceutically acceptable salts thereof wherein
 X is a carbonyl, sulfonyl, methylene, or methylene substituted with optionally substituted phenyl;
 Z is nitrogen or CH;
 $Ar_1$ and $Ar_2$ independently represent aryl groups; and
 Y is hydrogen; or
 Y and $R_1$ or $R_2$ together represent $CH_2$; $CH_2CH_2$; $CH_2O$; $CH_2S$ forming a five or six membered ring and such ring may be optionally substituted with loweralkyl or phenyl; or pharmaceutically acceptable salts thereof, useful in the treatment of neoplastic diseases, and bacterial or fungal infections, and for preventing or decreasing the production of abnormally phosphorylated paired helical filament (PHF) epitopes associated with Alzheimer's Disease and, therefore for treating Alzheimer's Disease.

1 Claim, 5 Drawing Sheets

FIG. 1
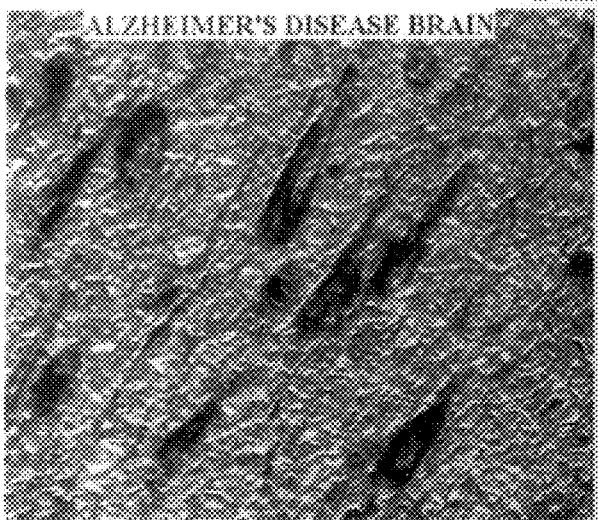
FIG 1A
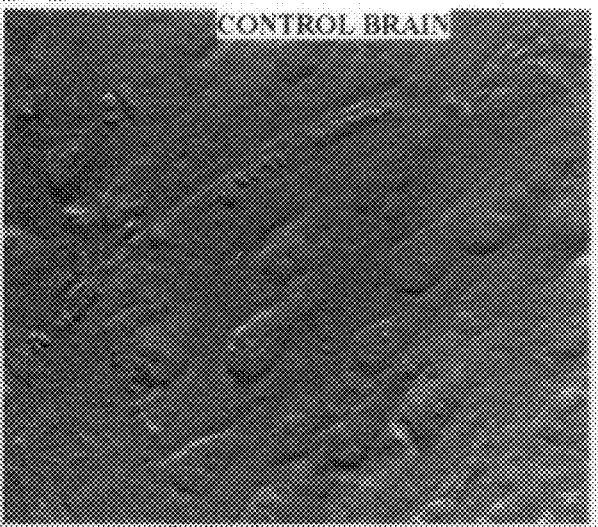
FIG 1B
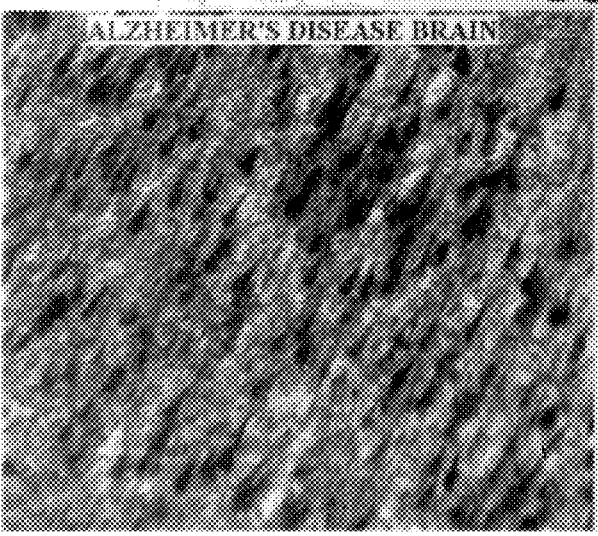
FIG 1C
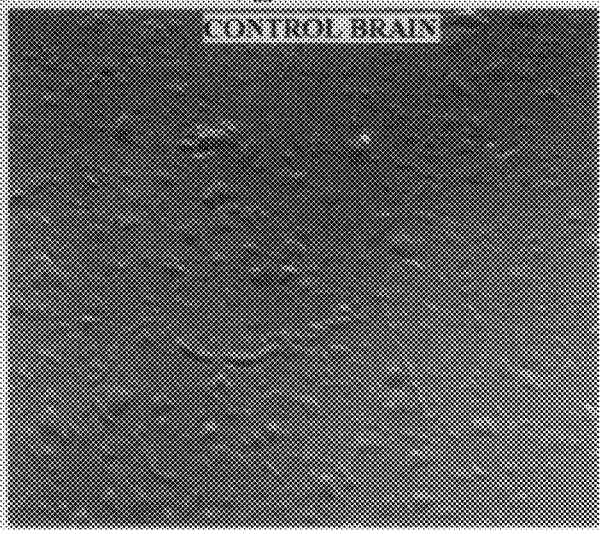
FIG 1D

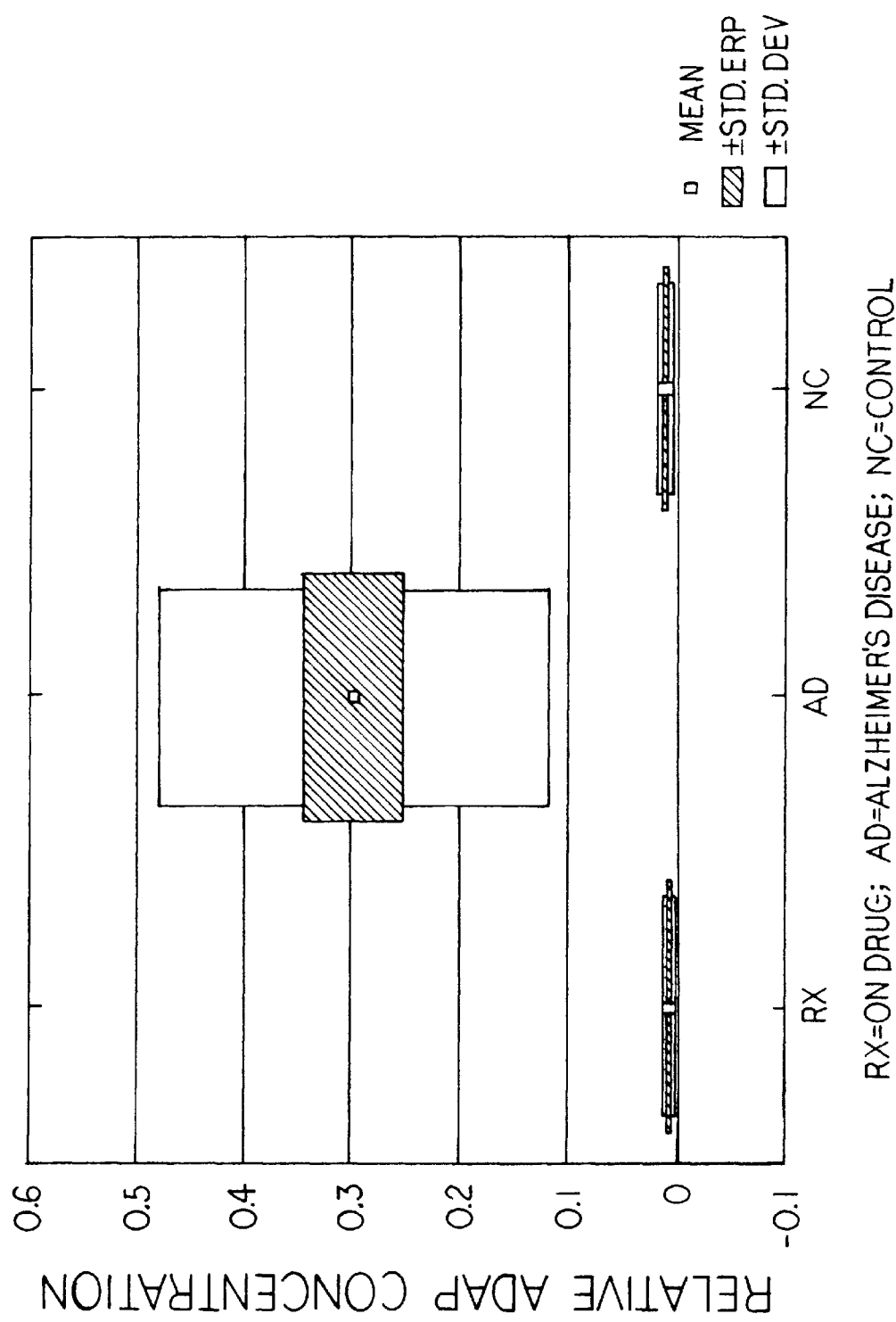

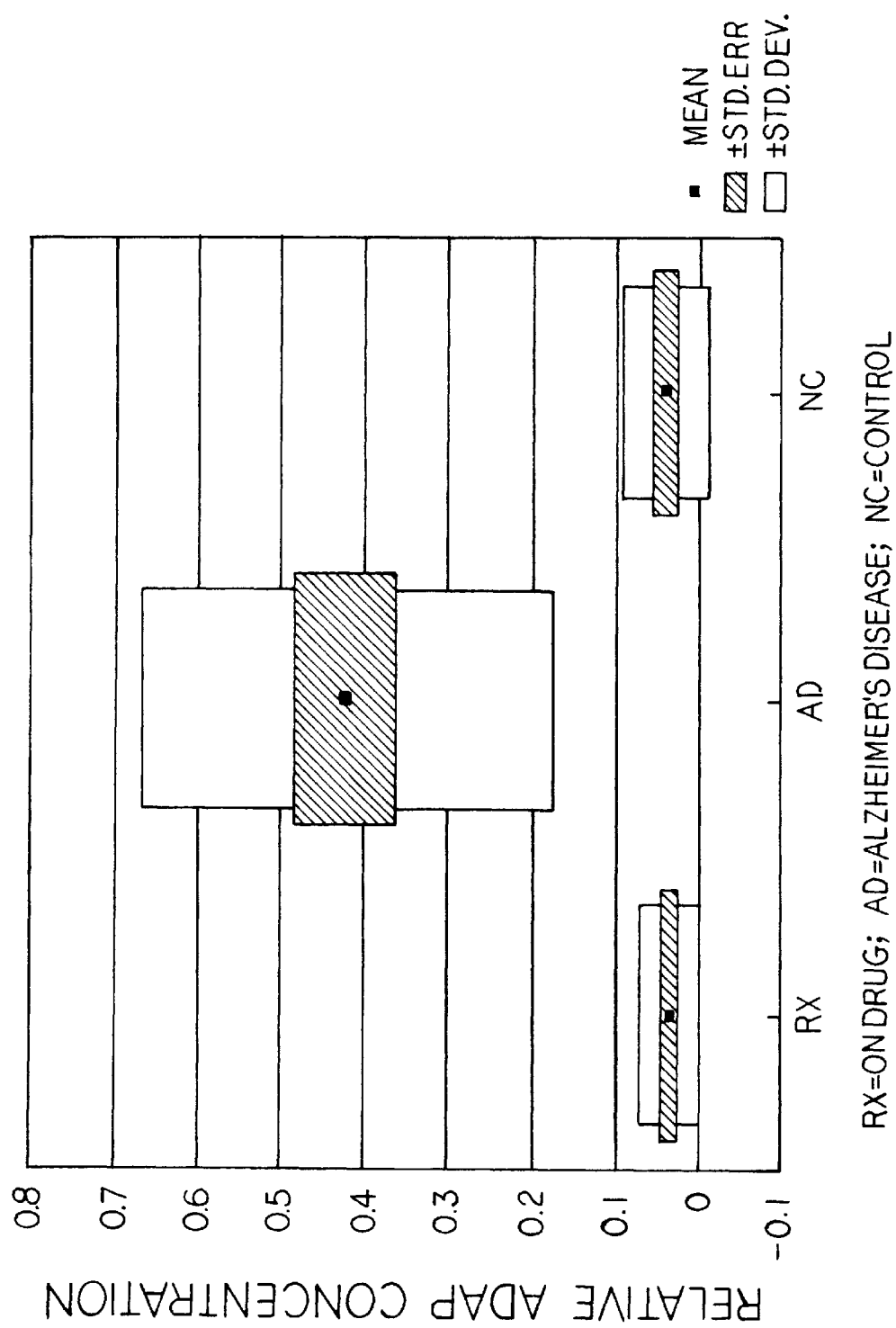

CERTAIN SUBSTITUTED 1-ARYL-3-PIPERAZIN-1'-YL PROPANONES

This is a continuation of application Ser. No. 08/341,481, filed Nov. 17, 1994, now U.S. Pat. No. 5,658,909.

BACKGROUND OF THE INVENTION

1. Field of the Invention

This invention relates to substituted 1-aryl-3-piperazin-1'-yl propanones and 1-aryl-3-piperidin-1'-yl propanones. These compounds are useful in the treatment of Alzheimer's Disease, neoplastic disease, and bacterial or fungal infections.

2. Description of the Related Art

Alzheimer's Disease is a progressive neurodegenerative disorder affecting 7% of the population over 65 years of age and characterized clinically by progressive loss of intellectual function. This impairment of function is caused by the presence of neuritic plaques in the neocortex and the loss of presynaptic markers of cholinergic neurons. Neuritic plaques are composed of degenerating axons and nerve terminals, often surrounding an amyloid core and usually containing reactive glial elements. Another characteristic pathologic feature of Alzheimer's Disease is the neurofibrillary tangle, which is an intraneuronal mass which corresponds to an accumulation of abnormally phosphorylated tau protein polymerized into fibrillar structures termed paired helical filaments. In addition, the neurofibrillary tangle also contains highly phosphorylated neurofilament proteins. Even the earliest papers on Alzheimer's Disease were clear that both "senile" plaques and neurofibrillary tangles had to be present in abundance to allow a post-mortem diagnosis of the disease. Before any understanding of the molecular nature of these structures was obtained, efforts were being made to understand the relationship between the numbers of these lesions and the progression or severity of the dementia experienced by the patient. The limitations of silver staining were such that early workers in this field were unable to appreciate the complexity of these abnormal structures (Ball, M J, Neurobiol. of Aging, 8: 564–565, 1987). Although early attempts to correlate pathologic lesion counts with clinical symptoms generally yielded poor results, it was clear that the incidence of large numbers of both type lesions were invariably associated with dementia (Perry et al, J. Neural Transmission, 24: 131–136, 1987; Alafuzoff, I., Acta Neuropath, 74: 209–225, 1987; Whitehouse et al, Prog. Clin. Biol. Res., 317: 131–142, 1989; Tomlinson, Neuropathol. Appl. Neurobiol, 15: 491–512, 1989).

More recent work has allowed a clearer definition of the nature of the lesions stained by silver salts. "Senile" plaques are actually two distinct types of structures, the classical plaques described by Alzheimer being composed of degenerating neuronal elements (neurites) surrounding a central core of amyloid, while the other so-called "diffuse" or "primitive" plaque is usually a deposit of amyloid without a halo of degenerating neurites (Tagliavini, , et al, Neurosci. Lett., 93, 191–196, 1988; Dickson, D W, et al, Am. J. Path., 132, 86–101, 1988). These structures are difficult to distinguish from each other with silver stains or with the widely used fluorescent dye, thioflavin S. Early attempts, using silver staining, at correlations between plaque number and extent of dementia, as well as some more recent studies using thioflavin S, were flawed by this inability to define what type of plaque was being counted (Hansen, L A, et al, Neurology, 38, 48–54, 1988; Katzman, R, et al, Ann. Neurol., 23, 138–144, 1988). This becomes very obvious in recent studies, which have consistently reported that amyloid plaques can be found in large numbers in the brains of the majority of the very elderly (over 80 years), and are only rarely associated with dementia when present without evidence of degenerating neurites (Davies, L, et al, Neurology, 38, 1688–1693, 1988; Delaere, P, et al, Neurosci. Lett., 116, 87–93, 1990; Dickson, D W, et al, Neurobiol. Aging, 13, 179–189, 1991).

The counting of neurofibrillary tangles also fails to give an accurate picture of the extent of neurofibrillary degeneration. Again, the presence of large numbers of tangles is invariably associated with a profound dementia, and some index of disease severity can be gained from tangle counts (Tomlinson, B E, Neuropathol. Appl. Neurobiol., 15, 491–512, 1989; Delaere, P, et al, Acta Neuropath., 77, 645–653, 1989). Electron microscopy first revealed that tangles were composed of masses of paired helical filaments (PHF) filling the cytoplasm of neurons (Terry, R D, et al, pages 145–155, In CIBA Foundation Symposium on Alzheimer's Disease and Related Conditions. Ed. by Wolstenholme, GEW, O'Conner, M, J and A Churchill, London, 1970). These studies also clearly showed that degenerating neurites also contained PHF, a fact only widely appreciated much later, when the use of antibodies to PHF became common (Wolozin, B L, et al, Science, 232, 648–650, 1986). Thus, both the plaques and the tangles of Alzheimer's Disease contain PHF. The use of antibodies to PHF also revealed the widespread presence of these paired helical filaments in neuronal processes (Brun, A, Prog. Clin. Biol. Res., 317, 285–293, 1989). Thus, the presence of PHF is much more widespread than was first suspected, and is today considered to be an indication of a widespread neuronal disease, of which the neuritic plaque and the neurofibrillary tangle are only the most obvious signs (McKee, A C, et al, Ann. Neurol., 30, 156–165, 1991). It has been estimated that as much as 90% of the PHF in the cortex of the average Alzheimer case is present in neuronal processes rather than in the plaque or tangle (Wolozin, B L, Ann. Neurol., 22, 521–526, 1987). Much of the early and indeed the present confusion with regard to diagnosis and severity of Alzheimer's Disease comes from the failure to appreciate the complexity of the pathology in this disease, although the occurrence of significant amounts of PHF in the brain is always associated with severe dementia (Hyman, B T, Current Opinions in Neurology and Neurosurgery, 5, 88–93, 1992). These results suggest that good correlations can be obtained between the concentration of PHF proteins (sometimes referred to as Alzheimer's Disease Associated Proteins or ADAP) in the cerebral cortex and the degree of dementia measured prior to the death of the patient (Ghanbari, H A, et al, JAMA, 263, 2907–2910, 1990).

It is noted that the terminology used to describe the abnormal protein complexes composing the fibrillar pathology in Alzheimer's Disease can be confusing. PHF is a morphological designation, describing abnormal filaments found in neurofibrillary tangles. An abnormal protein species migrating at 68 kDa, electrophoretically, and observed on immunoblots of tissue from AD brains was termed A68 (Wolozin, B, et al, Science, 232, 648–650, 1986). A protein complex shown to be specific for AD by immunochemical analyses was designated Alzheimer's Disease Associated Protein or by the acronym, ADAP (Ghanbari, H A, et al, JAMA, 263, 2907–2910, 1990). It is now known that A68 and ADAP, when viewed by the electron microscope, are PHFs. These PHFs have been further shown to contain, primarily, the microtubule-associated protein, tau. Hence, the terms A68, ADAP, PHF and PHF-tau are often used interchangeably. Thus, they are meant to be interchangable herein.

A series of important studies have suggested that the progression of Alzheimer's Disease can be defined pathologically by careful neuroanatomic studies of large numbers of brains from elderly humans, (Braak, H, et al, Neurosci. Lett., 103, 24–28, 1989; Braak, H, et al, Neuropath. and Applied Neurobiol., 15, 13–26, 1989; Braak, H, et al, Acta Neuropath., 82, 239–259, 1991; Braak, H, et al, European Neurology, 33, 403–408, 1993). The Braak's focus is almost entirely on the development of neurofibrillary pathology, which begins in the entorhinal cortex perhaps years before the clinical signs of the disease are apparent. The progression of Alzheimer's Disease is thought to be somewhat unusual, in the sense that the disease progresses by the involvement of more and more neurons in the formation of PHF, in an anatomic sequence which is to some extent predictable. In the initial stages, only those neurons of the entorhinal cortex contain PHF, in later stages, neurons of the CA1 and CA2 pyramidal layer of the hippocampus contain these structures, and still later, neurons of the association cortex begin to show evidence of PHF formation. Clearly, prevention of PHF formation even after the process is underway in the hippocampus could limit the disease to this brain region, at which point clinical problems are confined to some loss of short term memory. Patients first seek help at a stage when PHF pathology is largely limited to the hippocampus (Berg, L, et al, pages 9–25, in Alzheimer's Disease, Eds., Terry, R D; Katzman, R; Bick, K L. Raven Press, New York, 1994). To prevent the progression of Alzheimer's Disease at this point would clearly be a major benefit to the patient (Davies, P, pages 327–334, in Alzheimer's Disease, Eds., Terry, R D; Katzman, R; Bick, K L. Raven Press, New York, 1994; Khachaturian Z S, et al, pages 445–454, in Alzheimer's Disease, Eds., Terry, R D; Katzman, R; Bick, K L. Raven Press, New York, 1994).

Attempts to determine the molecular nature of the PHF were hampered at first by an approach which attempted to purify PHF from isolated neurofibrillary tangles. Once incorporated into the macromolecular complex that is the tangle, PHFs become extremely difficult to solubilize for protein analysis. The microtubule-associated protein tau appears to be a major antigenic component of PHF. The repeat region of microtubule-associated protein tau forms part of the core of the paired helical filament of Alzheimer's Disease (Goedert, M, et al, Proc. Nat'l. Acad. Sci., 85, 4051–4055, 1988; Wischik, C M, et al, Proc. Nat'l. Acad. Sci., 85, 4506–4510, 1988).

The involvement of protein phosphorylation in the formation of PHF has been suggested by a variety of studies which have shown that tau in PHF is hyperphosphorylated (Kosik, K S, et al, Ann. Med., 21, 109–112, 1989; Goedert, M, Trends in Neurosciences, 16, 460–465, 1993; Iqbal, K, et al, Act Neurobiologiae Experimentalis, 53, 325–335, 1993). There is suggestive evidence that several other proteins, especially neurofilaments and other microtubule associated proteins (MAPs) are also hyperphosphorylated in the brains of patients with Alzheimer's Disease (Lovestone, S, et al, Current Opinions in Neurology and Neurosurgery, 5, 883–888, 1992).

In 1985, a monoclonal antibody ALZ50 was raised (produced by hybridoma cell line ATCC No. HB9205) that recognized a 68 kDa polypeptide (termed A68) in immunoblots of the vulnerable brain regions in AD, but not in control brains, (Wolozin, B, et al, Science, 232, 648–650, 1986). Immunohistochemical analysis with this antibody indicated an intense reaction with neurofibrillary tangles and, in later experiments, with the PHF's, as well. The discovery of A68 was the first report of a biochemically determined abnormal protein species associated with the fibrillar pathology in AD.

In other laboratories in 1986, monoclonal and polyclonal antibodies recognizing the microtubule-associated protein, tau, were shown to react with neurofibrillary tangles and subsequently, with PHFs (Grundke-Iqbal, I, et al, Proc. Nat'l., Acad. Sci., 83, 4913–4917, 1986; Kosik, K S, et al, Proc. Nat'l. Acad. Sci., 83, 4044–4048, 1986). Furthermore, biochemical analyses of the protease-resistant "core" of the PHF demonstrated the presence of peptides containing the tau sequence, (Goedert, M, et al, Proc. Nat'l. Acad. Sci., 85, 4051–4055, 1988; Wischik, C M, et al, Proc. Nat'l. Acad. Sci., 85, 4506–4510, 1988). Additionally, monoclonal antibodies, whose epitopes spanned the tau molecule, all were shown to react with neurofibrillary tangles in AD brain (Kosik, K S, et al, Neuron, 1, 817–825, 1988). Much later, it was determined that the ALZ50 antibody reacts with the extreme amino terminus of the tau molecule, (Goedert, M, et al, Neuroscience Letters, 126, 149–154, 1991).

In 1990, in an attempt to purify A68, a more readily soluble preparation of PHFs was isolated (Greenberg, S and Davies, P, Proc. Nat'l. Acad. Sci., 87, 5827–5831, 1990). Immunoblots of these structures indicated that three closely migrating electrophoretic species, the slowest migrating of which was ca. 68 kDa in size, all reacted with ALZ50 and tau antibodies (Lee, V, et al, Science, 251, 675–678, 1991). This indicated that the A68 complex of proteins is, to a large extent, composed of the tau protein. This polymerized form of tau was shown over the years to be in a hyperphosphorylated state.

Other monoclonal antibodies raised against human PHF preparations are the antibodies PHF-1 and TG3. While these antibodies display robust affinity for paired helical filament preparations, they only have trace reactivity towards normal adult tau. Further studies revealed that the monoclonal antibody PHF-1 has a reduced affinity for PHF which has been treated with alkaline phosphatase or hydrofluoric acid, thereby suggesting that this antibody recognized a phosphorylated epitope(s) in paired helical filaments. These phosphorylated epitopes (recognized by PHF-1) reside within the C-terminal fragment of the tau protein, at serine 396 and 404 (Trojanowski, J. Q., et al, Clin. Neurosci., 1, 184–191, 1993). The epitope(s) recognized by TG3 has not been mapped yet.

To date, it has not been possible to consistently induce the formation of Alzheimer-like epitopes either in vivo or in vitro. Hence, there is a need for an assay for the determination of tau protein, paired helical filaments and mechanisms involved with Alzheimer's Disease. There is further a need for an assay suitable for screening for drugs which may prevent or decrease Alzheimer's Disease activity.

SUMMARY OF THE INVENTION

The compounds of this invention and an antipyschotic agent, chlorpromazine are active in an assay indicative of the potential of certain drugs to inhibit a hallmark trait of Alzheimer's Disease. Further, chlorpromazine is shown herein to be capable of treating and/or preventing Alzheimer's Disease. Consequently, the compounds of this invention are useful for treating and/or preventing the disease.

The human neuroblastoma MSN1a cell line expresses the proteins known to be involved in PHF formation (including tau, other MAPs and neurofilament proteins, and thus is a cell line in which Alzheimer's Disease epitopes can be expressed. (Arias et al, J. Neurochem., 61: 673–682, 1993; Vincent et al, J. Neurochem., 62: 715–723, 1994).

Immunohistochemical staining of brains from normal and Alzheimer's Disease (AD) patients using the monoclonal antibodies PHF-1 and TG3 indicates that these monoclonal antibodies specifically stain elements of AD brain, but not normal brain (FIG. 1). Conditions were established which led to hyperphosphorylation of the proteins known to be involved in PHF formation. Using monoclonal antibodies PHF-1 and TG3 generated to human PHF preparations, the effects of a variety of manipulations of the phosphorylation state of these proteins were tested. These tests required that most of the abnormal epitopes recognized by these monoclonal antibodies in the human Alzheimer brain should be generated in the MSN1a cells. The treatment of MSN1a cells with okadaic acid and other selected inhibitors of protein phosphatases has been found to generate the epitopes associated with these Alzheimer brain specific monoclonal antibodies, thereby meeting the requirements described above. These epitopes are either absent or present at a very low level in untreated MSN1a cells.

The AD specificity of the PHF-1 and TG3 antibodies was also demonstrated using an ELISA assay. Shown in FIG. 2A are bar graphs (percent of AD) of the ELISA immunoreactivity of brain preparations (AD or normal) to either PHF-1 or TG3. Shown in FIG. 2B are bar graphs (percent of MSN+) of the ELISA immunoreactivity of MSN1a cell preparations (minus or plus okadaic acid) to either PHF-1 or TG3. The MSN1a cell preparations plus vs minus okadaic acid closely parallel the AD vs normal brain preparations. This clearly shows the relationship between disease pathology (i.e. AD brain) and what is recognized by the antibodies in the MSN1a in vitro cell culture assay. The cell culture system according to the invention in which epitopes characteristic of PHF can be readily generated and subsequently recognized by the specific Alzheimer brain specific antibodies provides an assay suitable for screening compounds for their ability to block the production of these phosphorylated epitopes.

PHF tau protein has lower affinity for microtubules as compared to normal tau protein, which is likely the result of the abnormal phosphorylation (Lindwall et al, J. Biol. Chem., 259: 5301–5305, 1984). As a consequence, microtubule destabilization occurs which interferes with important neuronal processes such as rapid axonal transport and, subsequently, this process leads to the formation of PHF and the neurofibrillary tangles (Bancher, et al, Brain Res., 477, 90–99, 1989). Thus, inhibition of the production of the abnormal phosphorylated PHF epitopes will interfere with and/or prevent the formation of PHF. Since PHF formation is a major feature of Alzheimer pathology, the development of compounds that interfere with all or part of this process inhibit or prevent the progression of this disease.

The invention provides compounds of formula I:

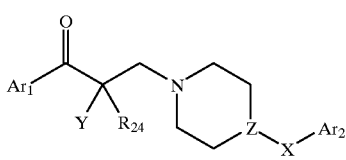

I or the pharmaceutically acceptable salts thereof wherein
X is a carbonyl, sulfonyl, methylene, or methylene substituted with optionally substituted phenyl; and
Z is nitrogen or CH; and
$Ar_1$ and $Ar_2$ independently represent aryl groups; and
$R_{24}$ is hydrogen; or when Y is other than hydrogen $R_{24}$ is hydrogen, loweralkyl, or optionally substituted phenyl; and
Y is hydrogen, straight or branched chain alkyl having 1–6 carbon atoms; or Y and a substituent on the $Ar_1$ group together represent $CH_2$, $CH_2CH_2$, $CH_2O$, or $CH_2S$ to form a five or six membered ring where the ring is optionally substituted with loweralkyl or phenyl.

These compounds are useful for treating Alzheimer's Disease, neoplastic disease, and bacterial or fungal infections. Thus, these compounds are antineoplastic, antibacterial, and antifungal agents.

The compounds of this invention, by preventing or decreasing the production of abnormally phosphorylated paired helical filament epitopes associated with the production of the neurofibrillary tangles, a characteristic pathological feature of Alzheimer's Disease, are useful in the treatment of this neurodegenerative disorder.

The compounds of formula I inhibit and/or prevent the formation of abnormally phosphorylated epitopes on PHF tau. Through inhibitory interactions of the phosphorylation events associated with the formation of PHF tau, and other proteins involved in PHF formation, one can modulate the assembly of microtubules, thereby affecting neuronal processes such a rapid axonal transport, thus preventing the formation of PHF and the production of the neurofibrillary tangles. Thus, the compounds of the present invention are therapeutically useful in various neurodegenerative disorders such as Alzheimer's Disease. In addition, the compounds of the present invention are useful for the treatment of certain neoplastic diseases, and can be used as antibacterial and antifungal agents.

Thus, the invention provides methods of preventing and/or treating Alzheimer's Disease in a patient comprising administering to the patient a compound of formula I in an amount effective to inhibit formation of abnormally phosphorylated paired helical filament epitopes. More specifically, these methods involve administering the compound to a patient susceptible to Alzheimer's Disease or suffering from or affected by the disease or manifesting its clinical symptoms.

BRIEF DESCRIPTION OF THE DRAWINGS

FIGS. 1A–1D are images produced by light microscopy showing immunohistochemical staining of brain tissue from normal Alzheimer's Disease patients with monoclonal antibodies PHF-1 and TG3.

FIG. 4A is a chart showing relative ADAP concentrations in Brodman Area 10 in Alzheimer's Disease patients, normal controls and patients treated with chlorpromazine (Rx).

FIG. 4B is a chart showing relative ADAP concentrations in Brodman Area 38 in Alzheimer's Disease patients, normal controls and patients treated with chlorpromazine (Rx).

DETAILED DESCRIPTION OF THE INVENTION

Figure 2A:
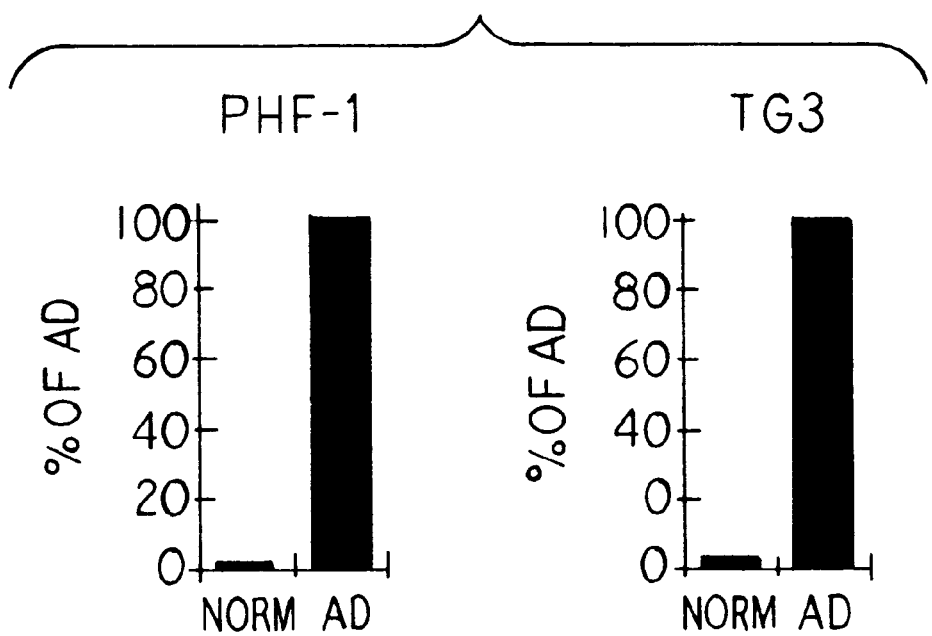
FIG. 2A is a graphic comparison of normal (Norm) and Alzheimer's Disease (AD) brain homogenate immunoreactivity toward PHF-1 and TG3 antibodies expressed as a percent of total AD immuonreactivity.

The invention provides compounds of formula I or the pharmaceutically acceptable salts thereof wherein
X represents carbonyl, sulfonyl, methylene, or methylene substituted with optionally substituted phenyl;
Z is nitrogen or CH;

$Ar_1$ is a group of the formula:

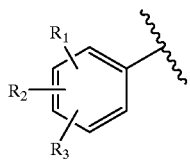

wherein $R_1$, $R_2$ and $R_3$ independently represent hydrogen, halogen, optionally substituted phenyl, loweralkyl, loweralkoxy, hydroxy, nitro, trifluoroalkyl, thioloweralkoxy, cyclohexyl, amino, acetyl, morpholino, cyano, piperidinyl, trifluoroalkoxy, alkylsulfonylamino, optionally substituted phenylethynyl, 4,5-dihaloimidazole, optionally substituted phenoxy, optionally substituted phenyl amino, or optionally substituted phenylsulfide, or two of $R_1$, $R_2$ and $R_3$ taken together can form an ethylenedioxy, ethyleneoxy, methylenedioxy or a lower straight chain alkyl bridge of 3–5 atoms optionally substituted by loweralkyl; or $R_1$, $R_2$ and $R_3$ are the same or different and represent a group of the formula:

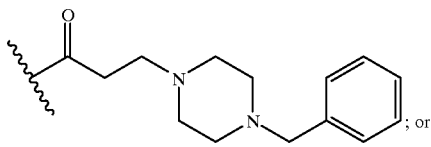

; or $Ar_1$ is a group of the formula:

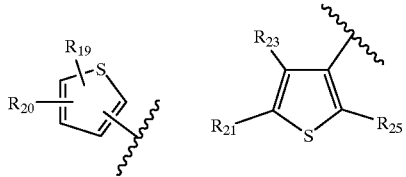

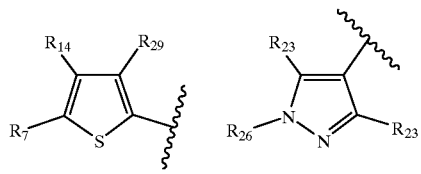

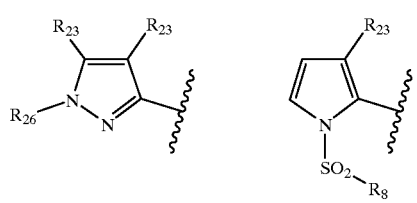

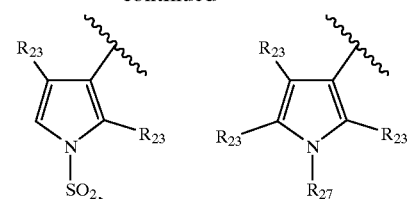

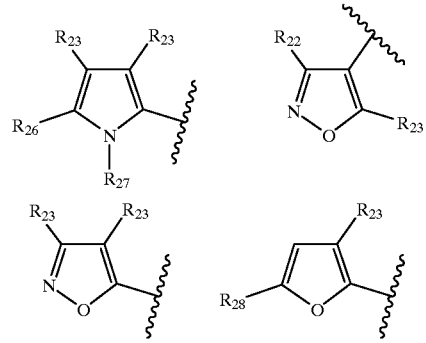

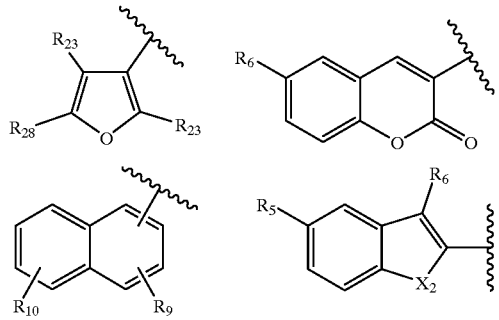

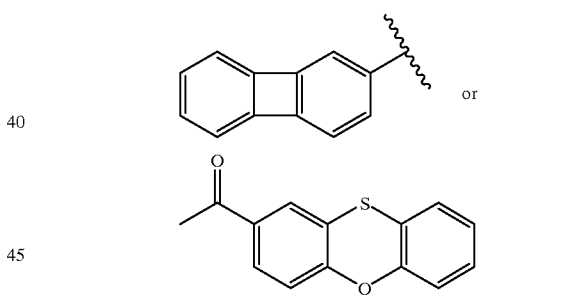

wherein $X_2$ is oxygen or sulfur $R_5$ is hydrogen, halo, loweralkyl, loweralkoxy or thioloweralkoxy;

$R_6$ is hydrogen, halo, or loweralkyl;

$R_7$ is hydrogen, loweralkyl, halo, nitro, cyano, optionally substituted thienyl, optionally substituted phenyl, morpholino, piperidinyl, piperazinyl, optionally substituted phenylmethylenylpiperazinyl, optionally substituted phenylsulfonylpiperazinyl, or optionally substituted phenylcarbonylpiperazinyl;

$R_8$ is loweralkyl or phenyl;

$R_9$ and $R_{10}$ are independently selected from hydrogen, halo, loweralkoxy, hydroxy;

$R_{14}$ is selected from hydrogen, loweralkyl, nitro or halo;

$R_{19}$ and $R_{20}$ are independently selected from hydrogen, loweralkyl, halo, nitro or optionally substituted phenyl;

$R_{21}$ is hydrogen, loweralkyl, nitro, halo, cyano, thienyl, phenyl, or phenylethynyl;

$R_{22}$ is hydrogen, carbomethoxy, phenyl, optionally substituted phenyl or loweralkyl;

$R_{23}$ is hydrogen or loweralkoxy;

$R_{24}$ is hydrogen; or when Y is other than hydrogen $R_{24}$ is hydrogen, loweralkyl, or optionally substituted phenyl;

$R_{25}$ is hydrogen, loweralkyl or thioalkoxy;

$R_{26}$ is loweralkyl, optionally substituted phenyl or optionally substituted phenylmethylenyl; and $R_{27}$ is loweralkyl, optionally substituted phenyl or optionally substituted phenylmethylenyl; and $R_{28}$ is hydrogen, optionally substituted phenyl, loweralkyl, or optionally substituted thienyl; and $R_{29}$ is hydrogen, nitro, or loweralkyl; and $Ar_2$ is a group of the formula:

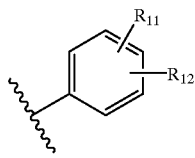

where $R_{11}$ and $R_{12}$ independently represent hydrogen, halo, trifluoromethyl, amino, nitro, cyano, acetyl, thioloweralkoxy, or loweralkyl;

or $R_{11}$ and $R_{12}$ together form a methylenedioxy or ethylenedioxy bridge; or $Ar_2$ is naphthyl, optionally substituted thienyl, furyl, 1,2,3-thiadiazolyl, or a group of the formula:

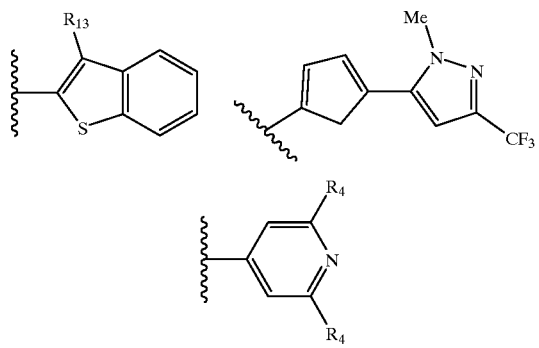

wherein $R_4$ independently represents hydrogen, halo, or loweralkyl;

$R_{13}$ is selected from hydrogen or halo; and

Y is hydrogen, straight or branched chain alkyl having 1–6 carbon atoms; or Y and $R_1$ $R_2$, $R_3$, $R_{19}$, $R_{20}$, $R_{22}$, $R_{23}$, or $R_{29}$ together represent $CH_2$; $C(R_{24})_2CH_2$; $C(R_{24})_2O$; or $C(R_{24})_2S$ forming a five or six membered ring.

The invention further provides compounds of formula II:

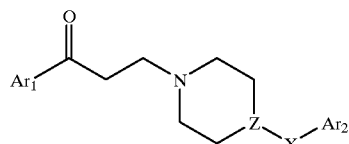

wherein

X represents carbonyl, sulfonyl, or methylene;

Z is nitrogen or CH;

$Ar_1$ is a group of the formula:

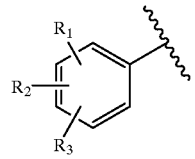

wherein $R_1$, $R_2$ and $R_3$ independently represent hydrogen, phenyl, nitro, halogen, loweralkyl, loweralkoxy, hydroxy, trifluoroalkyl, thioloweralkoxy, cyclohexyl, amino, acetyl, morpholino, cyano, piperidinyl, trifluoroalkoxy, alkylsulfonylamino, optionally substituted phenylethynyl, 4,5-dihaloimidazole, optionally substituted phenyl amino, optionally substituted phenoxy, optionally substituted phenylsulfide, or taken together form a methylenedioxy bridge, or $Ar_1$ is a group of the formula:

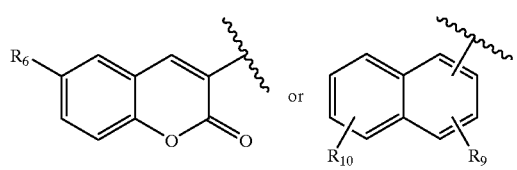

wherein $R_6$ is hydrogen, halo, or loweralkyl;

$R_9$ and $R_{10}$ are independently selected from hydrogen, halo, loweralkoxy, hydroxy; and $Ar_2$ is a group of the formula:

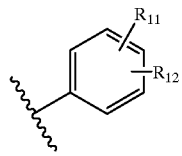

where $R_{11}$ and $R_{12}$ independently represent hydrogen, halo, trifluoromethyl, amino, nitro, cyano, acetyl, thioloweralkoxy, loweralkyl, or taken together form a methylenedioxy bridge.

The invention also provides compounds of formula III:

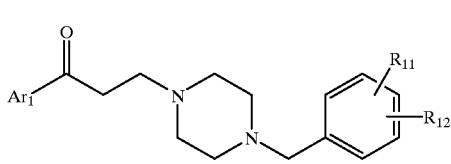

III wherein $R_{11}$ and $R_{12}$ independently represent hydrogen, halo, trifluoromethyl, nitro, cyano, acetyl, amino, thioloweralkoxy, loweralkyl, or taken together form a methylenedioxy bridge;

Ar₁ is a group of the formula:

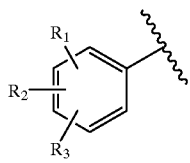

wherein

R₁, R₂ and R₃ independently represent hydrogen, phenyl, nitro, halogen, loweralkoxy, hydroxy, trifluoroalkyl, thioloweralkoxy, cyclohexyl, acetyl, amino, morpholino, cyano, piperidinyl, loweralkyl, trifluoroalkoxy, arylsulfonylamine, alkylsulfonylamino, optionally substituted phenylethynyl, 4,5-dihaloimidazole, optionally substituted phenoxy, or optionally substituted phenylsulfide, or R₁, R₂ and R₃ are the same or different and represent a group of the formula:

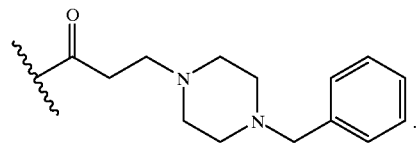

The invention further encompasses compounds of Formula IV:

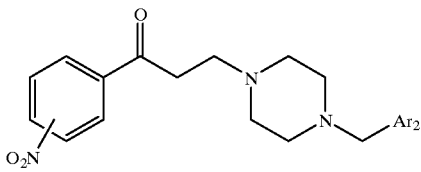

wherein Ar₂ represents phenyl or phenyl mono or disubstituted with halogen, cyano, nitro; or optionally substituted thienyl groups.

The invention further encompasses compounds of Formula V:

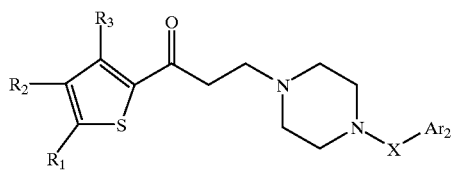

wherein

X represents carbonyl, sulfonyl, or methylene; and

R₁ represents hydrogen, loweralkyl, halogen, cyano, nitro, optionally substituted thienyl, optionally substituted phenyl, morpholino, piperidinyl, piperazinyl, optionally substituted phenylmethylenylpiperazinyl, optionally substituted phenylsulfonylpiperazinyl, or optionally substituted phenylcarbonylpiperazinyl; and R₂ is hydrogen, nitro, loweralkyl or halogen; and R₃ is hydrogen, nitro, or loweralkyl; and Ar₂ represents thienyl, phenyl or phenyl mono or disubstituted with halogen, cyano, nitro, loweralkyl, or loweralkoxy groups; or Ar₂ is a group of the formula:

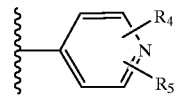

wherein R₄ and R₅ are independently selected from hydrogen, halo, or loweralkyl groups.

The invention further encompasses compounds of Formula VI:

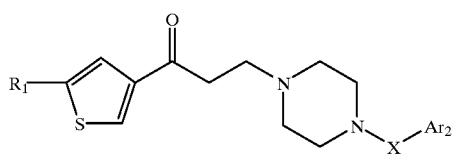

wherein

X represents carbonyl, sulfonyl, or methylene; and

R₁ represents halogen, loweralkyl, nitro, or cyano; and

Ar₂ represents phenyl or phenyl mono or disubstituted with halogen, cyano, or nitro groups.

The invention further encompasses compounds of Formula VII:

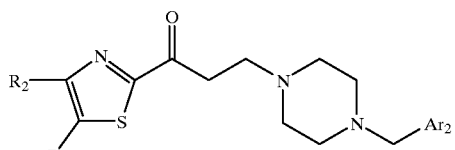

wherein

R1 and R2 are independently selected from hydrogen, halogen, loweralkyl, nitro, or optionally substituted phenyl; and Ar₂ represents phenyl or phenyl mono or disubstituted with halogen, cyano, nitro, loweralkyl or loweralkoxy groups.

The invention further encompasses compounds of Formula VIII:

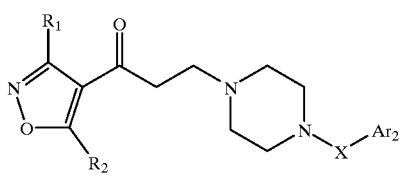

wherein

X represents carbonyl, or methylene; and

R₁ represents hydrogen, optionally substituted phenyl, carbomethoxy, or loweralkyl; and R₂ hydrogen, or loweralkyl; and Ar₂ represents phenyl or phenyl substituted with halogen, cyano, nitro, loweralkyl, or loweralkoxy groups.

The invention further encompasses compounds of Formula IX:

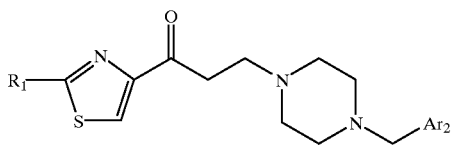

IX wherein
R$_1$ represents hydrogen, phenyl, or phenyl substituted with halogen, cyano, or nitro groups; and
Ar$_2$ represents phenyl or phenyl substituted with halogen, cyano, nitro, loweralkyl, or loweralkoxy groups.

The invention further encompasses compounds of Formula X:

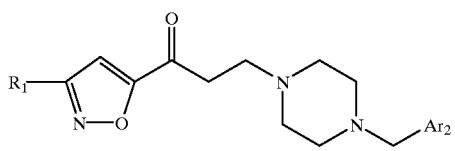

X wherein
R$_1$ represents hydrogen, optionally substituted phenyl, carbomethoxy, or loweralykyl groups; and
Ar$_2$ represents phenyl or phenyl substituted with halogen, cyano, nitro, loweralkyl, or loweralkoxy groups.

The invention further encompasses compounds of Formula XI:

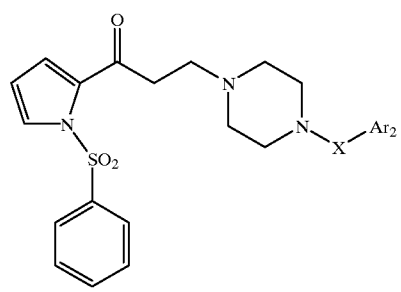

XI wherein
X represents carbonyl, sulfonyl, or methylene; and
Ar$_2$ represents phenyl or phenyl substituted with halogen, cyano, nitro, loweralkyl, or loweralkoxy groups.

The invention further encompasses compounds of Formula XII:

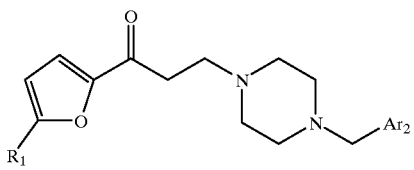

XII wherein
R$_1$ represents hydrogen, halo, optionally substituted phenyl, optionally substituted thienyl or loweralykyl groups; and Ar$_2$ represents phenyl or phenyl substituted with halogen, cyano, nitro, loweralkyl, or loweralkoxy groups.

The invention further encompasses compounds of Formula XIII:

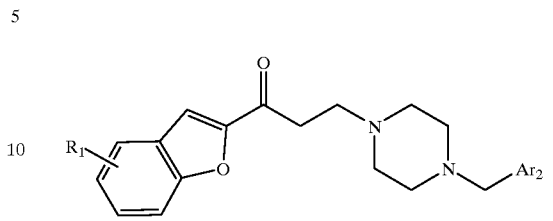

XIII wherein
R$_1$ represents hydrogen, halo, cyano, loweralykyl, or loweralkoxy groups; and
Ar$_2$ represents phenyl or phenyl substituted with halogen, cyano, nitro, loweralkyl, or loweralkoxy groups.

The invention further encompasses compounds of Formula XIV:

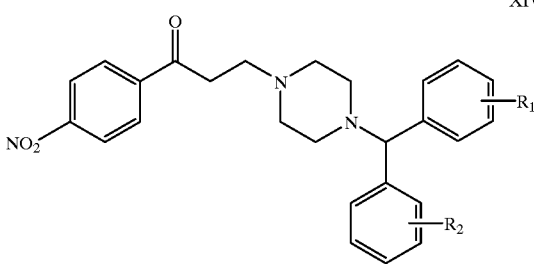

XIV wherein
R$_1$ and R$_2$ independently represent hydrogen or halogen.

The invention further encompasses compounds of Formula XV:

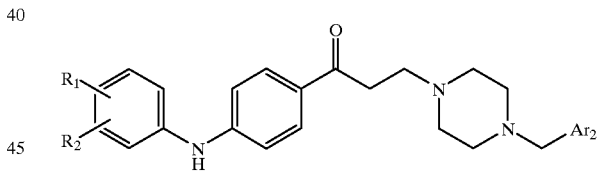

XV wherein
R$_1$ and R$_2$ independently represent hydrogen, nitro or halogen; and
Ar$_2$ represents phenyl or phenyl substituted with halogen, cyano, or nitro groups.

The invention further encompasses compounds of Formula XVI:

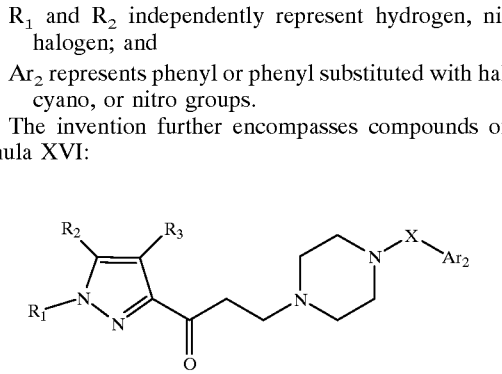

XVI wherein
R$_1$ is loweralkyl, optionally substituted phenyl, or optionally substituted phenylmethylenyl; and $R_2$ and $R_3$ are hydrogen or lower alkyl; and X represents carbonyl, sulfonyl, or methylene; and $Ar_2$ represents phenyl or phenyl substituted with halogen, cyano, nitro, loweralkyl, or loweralkoxy groups.

The invention further encompasses compounds of Formula XVII:

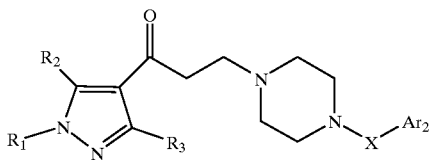

XVII wherein $R_1$ is loweralkyl, optionally substituted phenyl, or optionally substituted phenylmethylenyl; and $R_2$ and $R_3$ are hydrogen or lower alkyl; and X represents carbonyl, sulfonyl, or methylene; and $Ar_2$ represents phenyl or phenyl substituted with halogen, cyano, nitro, loweralkyl, or loweralkoxy groups.

The invention further encompasses compounds of Formula XVIII:

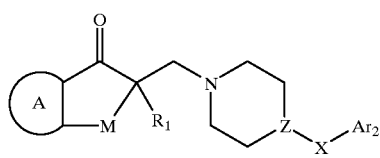

XVIII wherein

Z is CH or nitrogen;

X is carbonyl, sulfonyl, or methylene;

M is $CH_2$, $C(R_1)_2CH_2$, $C(R_1)_2O$, or $C(R_1)_2S$;

$R_1$ is hydrogen, loweralkyl, optionally substituted phenyl;

$Ar_2$ is optionally substituted phenyl, optionally substituted thienyl, or furyl; and

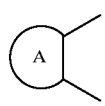

("the A ring") represents an aryl or heteroaryl ring having from zero to three hetero atoms selected from the group consisting of oxygen, sulfur and nitrogen.

Aryl and heteroaryl groups represented by the A ring are aromatic or heteroaromatic systems characterized by $4n+2\pi$ electrons.

The invention further encompasses compounds of Formula XIX:

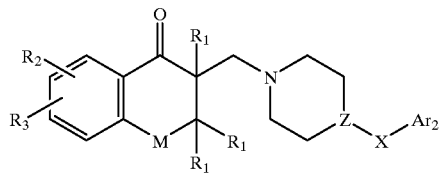

XIX wherein

Z is CH or nitrogen; and

X is carbonyl, sulfonyl, or methylene; and

M is $CH_2$, O, S, or a direct bond; and $R_1$ is hydrogen, loweralkyl, optionally substituted phenyl; and $R_2$ and $R_3$ are independently selected from hydrogen, halogen, loweralkyl, nitro, cyano, alkylsulfonamido, arylsulfonamido, optionally substituted phenyl, or $R_2$ and $R_3$ taken together represent a methylenedioxy ring; and $Ar_2$ is optionally substituted phenyl, optionally substituted thienyl, or furyl.

The invention further encompasses compounds of Formula XX:

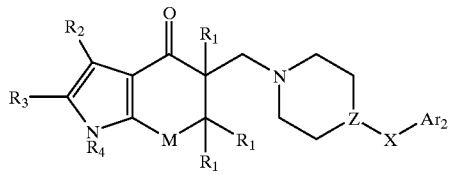

XX wherein

Z is CH or nitrogen; and

X is carbonyl, sulfonyl, or methylene; and

M is $CH_2$, O, S, or a direct bond; and $R_1$ is hydrogen, loweralkyl, optionally substituted phenyl; and $R_2$ and $R_3$ are independently selected from hydrogen, halogen, loweralkyl, nitro, cyano, or optionally substituted phenyl; and $R_4$ is hydrogen, loweralkyl, optionally substituted phenyl, or optionally substituted phenylmethylenyl; and $Ar_2$ is optionally substituted phenyl, optionally substituted thienyl, or furyl.

The invention further encompasses compounds of Formula XXI:

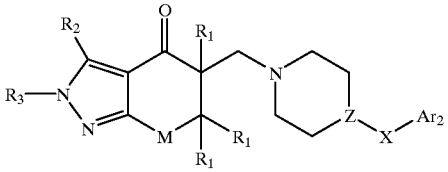

XXI wherein

Z is CH or nitrogen; and

X is carbonyl, sulfonyl, or methylene; and

M is $CH_2$, O, S, or a direct bond; and $R_1$ is hydrogen, loweralkyl, optionally substituted phenyl; and $R_2$ is hydrogen, halogen, loweralkyl, nitro, or cyano; and $R_3$ is hydrogen, loweralkyl, optionally substituted phenyl, or optionally substituted phenylmethylenyl; and $Ar_2$ is optionally substituted phenyl, optionally substituted thienyl, or furyl.

The invention further encompasses compounds of Formula XXII:

XXII wherein

Z is CH or nitrogen; and

X is carbonyl, sulfonyl, or methylene; and

M is $CH_2$, O, S, or a direct bond; and $R_1$ is hydrogen, loweralkyl, optionally substituted phenyl; and $R_2$ is hydrogen, halogen, loweralkyl, nitro, cyano, optionally substituted phenyl, alkylsulfonamido, arylsulfonamido, or thioloweralkyl; and $Ar_2$ is optionally substituted phenyl, optionally substituted thienyl, or furyl.

The invention further encompasses compounds of Formula XXIII:

XXIII wherein

Z is CH or nitrogen; and

X is carbonyl, sulfonyl, or methylene; and

M is $CH_2$, O, S, or a direct bond; and $R_1$ is hydrogen, loweralkyl, optionally substituted phenyl; and $R_2$ is hydrogen, halogen, loweralkyl, nitro, cyano, optionally substituted phenyl, alkylsulfonamido, arylsulfonamido, or thioloweralkyl; and $Ar_2$ is optionally substituted phenyl, optionally substituted thienyl, or furyl.

The invention further encompasses compounds of Formula XXIV:

XXIV wherein

Z is CH or nitrogen; and

X is carbonyl, sulfonyl, or methylene; and

M is $CH_2$, O, S, or a direct bond; and $R_1$ is hydrogen, loweralkyl, optionally substituted phenyl; and Y is O or S; and $R_2$ and $R_3$ are independently selected from hydrogen, halogen, loweralkyl, nitro, cyano, or optionally substituted phenyl; and $Ar_2$ is optionally substituted phenyl, optionally substituted thienyl, or furyl.

The instant invention includes optically active compounds as well as racemic mixtures of such compounds. The invention further includes the pharmaceutically acceptable salts of such compounds or racemic mixtures. The invention still further includes pharmaceutical compositions comprising such compounds, salts thereof, or racemic mixtures thereof.

As used herein, the term "loweralkyl" means straight or branched chain saturated hydrocarbon radicals having 1 to 4 carbon atoms, such as methyl, ethyl, n-propyl, t-butyl and the like.

As used herein, the term "thioloweralkoxy" refers to $-SR_{15}$, wherein $R_{15}$ is loweralkyl.

As used herein, the term "halo or halogen" refers to fluorine, chlorine, bromine, or iodine.

As used herein, the term "aryl" refers to systems characterized by $4n+2\pi$ electrons, i.e., aromatic carbocyclic groups having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, hydroxy, lower alkyl, lower alkoxy, lower alkylthio, trifluoromethyl, lower acyloxy, aryl, and heteroaryl.

As used herein, the term "heteroaryl" means 5, 6, or 7 membered aromatic ring systems having at least one hetero atom selected from the group consisting of nitrogen, oxygen and sulfur. Examples of heteroaryl groups are pyridyl, pyrimidinyl, pyrrolo, pyrazolo, pyrazinyl, pyridazinyl, oxazolo, furanyl, quinoline, isoquinoline, thiazole, thiadiazole, isoxazole, and thienyl, which can optionally be unsubstituted or substituted with, e.g., halogen, hydroxy, lower alkyl, lower alkoxy, lower alkylthio, trifluoromethyl, lower acyloxy, cyano, nitro, aryl, and heteroaryl.

As used herein, the term "alkylsulfonylamino" means $R_{16}S(O)_2NR_{17}-$ wherein $R_{16}$ is loweralkyl, phenyl, or substituted phenyl, and $R_{17}$ is hydrogen, loweralkyl or $-SO_2R_{16}$.

As used herein, the term "trifluoroalkoxy" refers to $-R_{18}CF_3$, wherein $R_{18}$ denotes a loweralkoxy group as defined above, attached to the parent molecular moiety through the oxygen atom. Representatives of such groups include methleneoxy, ethyleneoxy and the like.

As used herein, the term "optionally substituted phenyl" refers to a phenyl ring having from zero to three substituents independently selected from loweralkyl, halogen, hydroxy, loweralkoxy, amino, thioloweralkoxy, nitro and cyano.

As used herein, the term "optionally substituted thienyl" refers to a thiophene ring with from zero to three substituents independently selected from loweralkyl, halo, phenyl, cyano and nitro.

As used herein, the term "optionally substituted phenoxy" refers to the phenoxy ring substituted as defined for optionally substituted phenyl.

As used herein, the term "optionally substituted phenylsulfide" refers to a thiophenyl ring substituted as defined from optionally substituted phenyl.

The term "pharmaceutically acceptable salts" refers to the pharmaceutically acceptable, relatively non-toxic, inorganic, or organic acid addition salts of the compounds of this invention. These salts can be prepared in situ during the final isolation and purification of the compounds or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, methanesulfonate, stearate, laurate, borate, benzoate, lactate, phosphate, tosylate, citrate, maleate, fumarate, succinate, tartrate, napsylate, lactobionate, and the like. It will be apparent to those skilled in the art that, depending upon the number of available amino groups for salt formation, the salt of this invention can be per N-salts.

The present invention also provides pharmaceutical compositions which comprise one or more of the compounds of formulae I–XXIV above formulated together with one or more non-toxic pharmaceutically acceptable carriers. The pharmaceutical compositions may be specifically formulated for oral administration in solid or liquid form, for parenteral injection, or for rectal administration.

The pharmaceutical compositions of this invention can be administered to humans and other animals orally, rectaly, parenterally (i.e. intravenously, intramuscularly, or subcutaneously), intracisternally, intravaginally, intraperitoneally, topically (as by powders, ointments, or drops), transdermally, bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alingnates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Ophthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved. Generally dosage levels of about 0.1 to about 200, more preferably of about 0.5 to about 150, and most preferably about 1 to about 125 mg of active compound per kilogram of body weight per day are administered orally to a mammalian patient suffering from Alzheimer's Disease, neoplastic disease, or bacterial or fungal infections. If desired, the effective daily dose may be divided into multiple doses for purposes of administration, e.g. two to four separate doses per day.

All documents e.g., patents and journal articles, cited above or below are hereby incorporated by reference in their entirety.

One skilled in the art will recognize that modifications may be made in the present invention without deviating from the spirit or scope of the invention. The invention is illustrated further by the following examples which are not to be construed as limiting the invention or scope of the specific procedures described herein.

GENERAL PROCEDURE

As is more fully explained in the following scheme and examples, the compounds of the invention may be prepared by adding an appropriate secondary amine (1 mole) to a solution of concentrated hydrochloric acid (2–5 moles) in sufficient isopropanol to achieve an amine concentration of about 0.1 M–0.4 M. To the solution of amine hydrochloride salt which has been formed in situ is added paraformaldehyde (1–2.2 moles) followed by the desired aryl or heteroarylketone (1.1–2 moles), and the resulting reaction mixture is then refluxed for about 12–72 hours. The reaction is cooled and the resulting solid is filtered and recrystallized from methanol or triturated with methanol or ethanol to afford the desired product.

The compounds of the invention may be prepared according to the reactions set forth in the following reaction scheme.

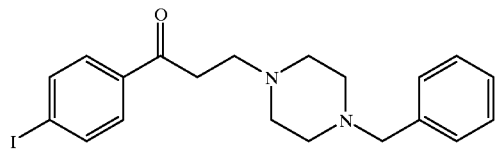

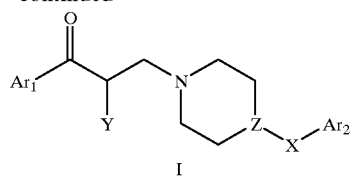

where $Ar_1$, $Ar_2$, X, Y, and Z are defined as for formula I above.

Using the above-described procedure, the compounds described in the following examples were prepared:

EXAMPLE 1

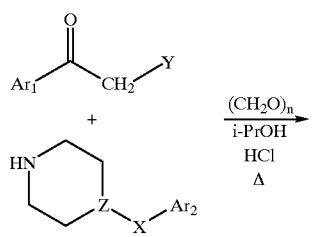

1-(p-Iodophenyl)-3-(4'-benzyl-1'-piperazinyl)-1-propanone dihydrochloride: mp 224° C. (dec.); $^1$H NMR (300 MHz, DMSO-$d_6$) δ 12.0 (brm, 2 H), 8.0 (d, 2 H), 7.65 (d, 2 H), 7.6 (m, 2 H), 7.45 (m, 3 H), 4.4 (brs, 2 H), 4.0–3.2 (m, 12 H).

EXAMPLE 2

1-(p-Fluorophenyl)-3-(4'-benzyl-1'-piperazinyl)-1-propanone dihydrochloride: mp >240° C.; $^1$H NMR of the free base (300 MHz, CDCl$_3$) δ 8.0 (m, 2 H), 7.3 (m, 5 H), 7.13 (t, 2 H), 3.5 (s, 2 H), 3.15 (t, 2 H), 2.85 (t, 2 H), 2.55 (brs, 8 H).

EXAMPLE 3

1-(3",4"-Dichlorophenyl)-3-(4'-benzyl-1'-piperazinyl)-1-propanone dihydrochloride: The solid was converted to its free base using NH$_4$OH, extracted with dichloromethane and purified via flash chromatography (Silica, EtOAc). The resulting oil was converted to its dihydrochloride salt by addition of dry ether-HCl to give the desired product: mp 220° C. (dec.); $^1$H NMR of the free base (300 MHz, CDCl$_3$) δ 8.03 (d, 1 H), 7.77 (dd, 1 H), 7.53 (d, 1 H), 7.3 (m, 5 H), 3.5 (s, 2 H), 3.12 (t, 2 H), 2.82 (t, 2 H), 2.5 (brs, 8 H).

EXAMPLE 4

1-(p-Chlorophenyl)-3-(4'-benzyl-1'-piperazinyl)-1-propanone dihydrochloride: mp >230° C.; $^1$H NMR of the free base (300 MHz, CDCl$_3$) δ 7.9 (d, 2 H), 7.43 (d, 2 H), 7.28 (m, 5 H), 3.5 (s, 2 H), 3.15 (t, 2 H), 2.83 (t, 2 H), 2.5 (brs, 8 H).

EXAMPLE 5

1-(p-Nitrophenyl)-3-(4'-benzyl-1'-piperazinyl)-1-propanone dihydrochloride: A mixture of p-nitroacetophenone (6.09 g, 0.037 mol), 1-benzylpiperazine (5.00 g, 0.023 mol), paraformaldehyde (1.11 g, 0.037 mol), and concentrated hydrochloric acid (7.00 mL, 0.084 mol) in 100 mL isopropanol were refluxed for 16 h. The reacton was cooled, filtered, and the filter cake was triturated with methanol (4x) to give 4.6 g (51%) of the desired product: mp 250° C.; $^1$H NMR (300 MHz, DMSO-$d_6$) δ 11.5 (brm, 2 H), 8.4 (d, 2 H), 8.2 (d, 2 H), 7.66–7.36 (m, 5 H), 4.3 (brm, 2 H), 3.8–3.2 (brm, 12 H).

EXAMPLE 6

1-(3"-Thienyl)-3-(4'-benzyl-1'-piperazinyl)-1-propanone dihydrochloride: mp 223° C.; $^1$H NMR (300 MHz, DMSO-d$_6$) δ 11.5 (brs, 2 H), 8.56 (s, 1 H), 7.8–7.3 (m, 7 H), 4.3 (brs, 2 H), 3.9–3.0 (brm, 12 H).

EXAMPLE 7

1-(2"-Thienyl)-3-(4'-benzyl-1'-piperazinyl)-1-propanone dihydrochloride: mp 240–241° C.; $^1$H NMR (300 MHz, D$_2$O) δ 7.82 (m, 2 H), 7.4 (brs, 5 H), 7.1 (m, 1 H), 4.3 (s, 2 H), 3.5 (brs, 12 H).

EXAMPLE 8

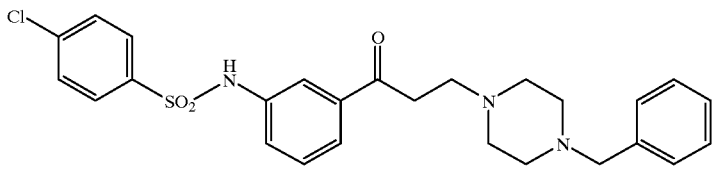

1-[3"-(p-Chlorophenyl)sulfonamidophenyl]-3-(4'-benzyl-1'-piperazinyl)-1-propanone dihydrochloride: mp 151–153° C.; $^1$H NMR (300 MHz, D$_2$O) δ 7.7–7.14 (m, 13 H), 4.2 (s, 2 H), 3.55–3.2 (brs, 12 H).

EXAMPLE 9

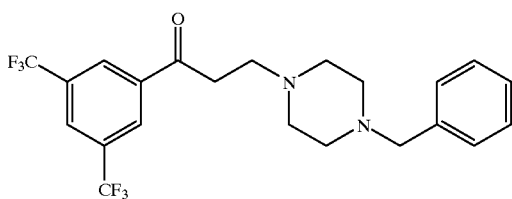

1-[3",5"-Bis-(trifluoromethyl)phenyl]-3-(4'-benzyl-1'-piperazinyl)-1-propanone dihydrochloride: The solid was basified with NH$_4$OH, extracted with dichloromethane and purified via flash chromatography (Silica, EtOAc). The free amine was converted to its dihydrochloride salt by the addition of dry ether-HCl: mp 255° C.; $^1$H NMR of the free base (300 MHz, CDCl$_3$) δ 8.38 (s, 2 H), 8.07 (s, 1 H), 7.29 (m, 5 H), 3.5 (s, 2 H), 3.23 (t, 2 H), 2.87 (t, 2 H), 2.5 (brm, 8 H).

EXAMPLE 10

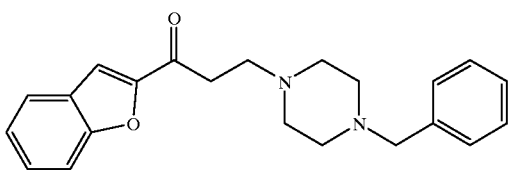

1-(Benzofur-2"-yl)-3-(4'-benzyl-1'-piperazinyl)-1-propanone dihydrochloride: mp 255–257° C.; $^1$H NMR (300 MHz, D$_2$O) δ 7.7 (m, 2 H), 7.55–7.18 (m, 8 H), 4.3 (s, 2 H), 3.5 (brs, 12 H).

EXAMPLE 11

1-(m-Nitrophenyl)-3-(4'-benzyl-1'-piperazinyl)-1-propanone dihydrochloride: mp 222° C. (dec.); $^1$H NMR (300 MHz, DMSO-d$_6$) δ 12.40–11.70 (brs, 2 H), 8.70 (s, 1 H), 8.50 (d, 1 H), 8.35 (d, 1 H), 7.90 (dd, 1 H), 7.85–7.35 (m, 5 H), 4.35 (brs, 2 H), 4.00–2.10 (m, 12 H).

EXAMPLE 12

1-(p-Methylphenyl)-3-(4'-benzyl-1'-piperazinyl)-1-propanone dihydrochloride: mp 196–198° C.; $^1$H NMR (300 MHz, CDCl$_3$) of the free base: δ 7.85 (d, 2 H), 7.40–7.10 (m, 7 H), 3.5 (s, 2 H), 3.15 (t, 2 H), 2.82 (t, 2 H), 2.65–2.40 (m, 8 H), 3.50 (s, 3 H).

EXAMPLE 13

1-(o-Fluorophenyl)-3-(4'-benzyl-1'-piperazinyl)-1-propanone dihydrochloride: mp 185–190° C.; $^1$H NMR (300 MHz, DMSO-d$_6$) δ 12.00–11.20 (brs, 2 H), 7.90–7.30 (m, 9 H), 4.35 (s, 2 H), 4.10–3.00 (m, 12 H).

EXAMPLE 14

1-(p-Methylthiophenyl)-3-(4'-benzyl-1'-piperazinyl)-1-propanone dihydrochloride: mp 216–220° C.; $^1$H NMR (300 MHz, DMSO-d$_6$) δ 12.10–11.70 (brs, 2 H), 7.95 (d, 2 H), 7.75–7.35 (m, 7 H), 4.35 (s, 2 H), 3.85–3.20 (m, 12 H), 2.75 (s, 3 H).

EXAMPLE 15

1-(m-Chlorophenyl)-3-(4'-benzyl-1'-piperazinyl)-1-propanone dihydrochloride: mp 196–199° C.; $^1$H NMR (300 MHz, DMSO-d$_6$) δ 12.30–11.55 (brs, 2 H), 8.15–7.30 (m, 9 H), 4.35 (brs, 2 H), 4.00–3.00 (m, 12 H).

EXAMPLE 16

1-(p-Bromophenyl)-3-(4'-benzyl-1'-piperazinyl)-1-propanone dihydrochloride: mp 205° C. (dec.); $^1$H NMR (300 MHz, DMSO-d$_6$) δ 12.00–11.20 (brs, 2 H), 7.90 (d, 2 H), 7.80 (d, 2 H), 7.70–7.35 (m, 5 H), 4.35 (brs, 2 H), 4.00–3.10 (m, 12 H).

EXAMPLE 17

1-(m-Nitrophenyl)-3-[4'-(p-fluorobenzyl)-1'-piperazinyl]-1-propanone dihydrochloride: mp 210° C. (dec.); $^1$H NMR (300 MHz, DMSO-d$_6$) δ 12.50–11.60 (brs, 2 H), 8.70 (s, 1 H), 8.55 (d, 1 H), 8.40 (d, 1 H), 7.90 (dd, 1 H), 7.80–7.60 (m, 2 H), 7.30 (m, 2 H), 4.35 (s, 2 H), 4.00–3.00 (m, 12 H).

EXAMPLE 18

1-(p-Trifluoromethoxyphenyl)-3-(4'-benzyl-1'-piperazinyl)-1-propanone dihydrochloride: mp 195° C. (dec.); $^1$H NMR (300 MHz, DMSO-d$_6$) δ 12.00–11.70 (brs, 2 H), 8.12 (dd, 2 H), 7.80–7.30 (m, 7 H), 4.40 (brs, 2 H), 3.85–3.10 (m, 12 H).

EXAMPLE 19

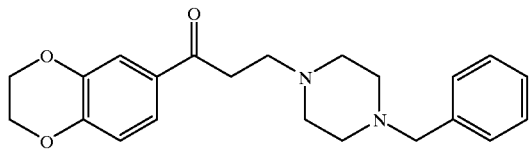

1-(2",3"-Dihydro-1",4"-benzodioxan-6"-yl)-3-(4'-benzyl-1'-piperazinyl)-1-propanone dihydrochloride: mp 215° C. (dec.); $^1$H NMR (300 MHz, DMSO-d$_6$) δ 11.85–11.60 (brs, 2 H), 7.65–7.30 (m, 7 H), 7.00 (d, 1 H), 4.70–4.20 (m, 4 H), 4.00–3.30 (m, 14 H).

EXAMPLE 20

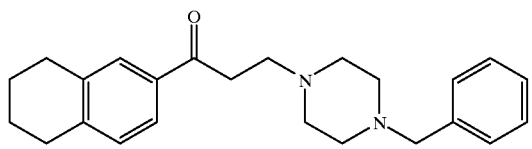

1-(1",2",3",4"-Tetrahydronaphth-6"-yl)-3-(4'-benzyl-1'-piperazinyl)-1-propanone dihydrochloride: mp 200° C. (dec.); $^1$H NMR (300 MHz, DMS-d$_6$) δ 12.35–11.70 (brs, 2 H), 7.80–7.15 (m, 8 H), 4.35 (brs, 2 H), 4.10–3.10 (m, 12 H), 2.90–2.65 (brs, 4 H), 1.70–1.90 (brs, 4 H).

EXAMPLE 21

1-(4"-Fluoronaphth-1"-yl)-3-(4'-benzyl-1'-piperazinyl)-1-propanone dihydrochloride: mp 220° C. (dec.); $^1$H NMR (300 MHz, DMSO-d$_6$) δ 12.50–11.80 (brs, 2 H), 8.75 (d,1 H), 8.40–8.10 (m, 2 H), 7.90–7.30 (m, 8 H), 4.45 (brs, 2 H), 4.10–3.10 (m, 12 H).

EXAMPLE 22

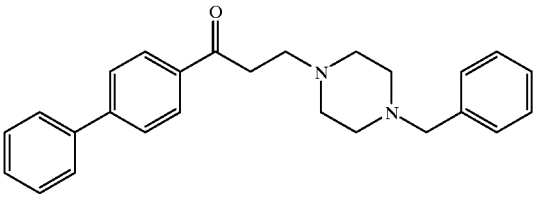

1-p-Biphenyl-3-(4'-benzyl-1'-piperazinyl)-1-propanone dihydrochloride: mp 225° C. (dec.); $^1$H NMR (300 MHz, DMSO-d$_6$) δ 12.55–11.50 (brs,2 H), 8.10 (d, 2 H), 7.90 (d, 2 H), 7.80–7.30 (m, 10 H), 4.35 (brs, 2 H), 4.00–3.10 (m, 12 H).

EXAMPLE 23

1-(m-Trifluoromethylphenyl)-3-(4'-benzyl-1'-piperazinyl)-1-propanone dihydrochloride: mp 215° C. (dec.); $^1$H NMR (300 MHz, DMSO-d$_6$) δ 12.20–11.00 (brs, 2 H), 8.55–8.00 (m, 2 H), 8.10 (d, 1 H), 7.85 (dd, 1 H), 7.70–7.40 (m, 5 H), 7.60–4.00 (brs, 2 H), 4.00–3.00 (m, 12).

EXAMPLE 24

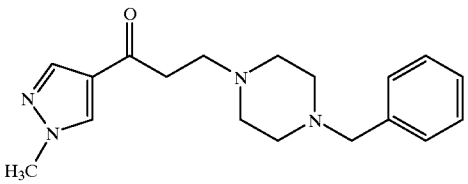

1-(1"-Methyl-1"-H-pyrazol-4"-yl)-3-(4'-benzyl-1'-piperazinyl)-1-propanone dihydrochloride: mp 221° C. (dec.); $^1$H NMR (300 MHz, DMSO-d$_6$) δ 12.45–11.60 (brs, 2 H), 8.45 (s, 1 H), 7.95 (s, 1 H), 7.75–7.30 (m, 5 H), 4.35 (brs, 2 H), 3.90 (s, 3 H), 3.80–3.10 (m, 12 H).

EXAMPLE 25

1-(p-Fluoro-m-bromophenyl)-3-(4'-benzyl-1'-piperazinyl)-1-propanone dihydrochloride: mp 220° C. (dec.); $^1$H NMR (300 MHz, DMSO-d$_6$) δ 12.40–11.40 (brs, 2 H), 8.32 (d, 1 H), 8.05 (m, 1 H), 7.80–7.30 (m, 6 H), 4.35 (brs, 2 H), 4.15–3.10 (m, 12 H).

EXAMPLE 26

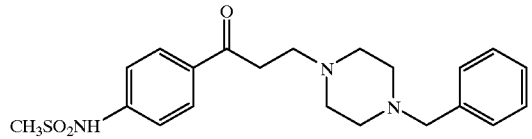

1-[p-(Methanesulfonamido)phenyl]-3-(4'-benzyl-1'-piperazinyl)-1-propanone dihydrochloride: mp 202–205° C.; $^1$H NMR (300 MHz, DMSO-d$_6$) δ 12.30–11.20 (brs, 2 H), 8.60 (d, 2 H), 7.75 (d, 2 H), 7.65–7.35 (m, 5 H), 4.33 (brs, 2 H), 4.06–310 (m, 12 H), 3.55 (s, 6 H).

EXAMPLE 27

1-(p-Cyclohexylphenyl)-3-(4'-benzyl-1'-piperazinyl)-1-propanone dihydrochloride: mp 231° C. (dec.); $^1$H NMR (300 MHz, DMSO-d$_6$) δ 12.40–12.10 (brs 1 H), 12.1–11.70 (brs 1 H), 7.90 (d, 2 H), 7.80–7.20 (m, 7 H), 4.70–4.20 (brs, 2 H), 4.20–3.10 (m 12 H), 2.70–2.40 (m, 2 H), 2.00–1.15 (m, 9 H).

EXAMPLE 28

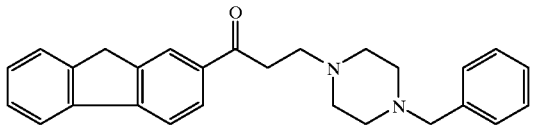

1-(Fluoren-2"-yl)-3-(4'-benzyl-1'-piperazinyl)-1-propanone dihydrochloride: mp 225° C. (dec.); $^1$H NMR (300 MHz, DMSO-d$_6$) δ 12.40–11.30 (brs, 2 H), 8.40–7.95 (m, 4 H), 7.75–7.30 (m, 8 H), 4.60–4.20 (brs, 2 H), 4.05 (s, 2 H), 3.95–3.05 (m, 12 H).

EXAMPLE 29

1-(p-Iodophenyl)-3-[4'-(o-fluorobenzyl)-1'-piperazinyl]-1-propanone dihydrochloride: mp215–217° C.; $^1$H NMR (300 MHz, DMSO-d$_6$) δ 11.6 (br, 2 H), 8.0 (d, 2 H), 7.7 (m, 3 H), 7.5 (m, 1 H), 7.3 (m, 2 H), 4.3 (brs, 2 H), 3.8–3.0 (brm, 12 H).

EXAMPLE 30

1-(o-Fluorophenyl)-3-[4'-(o-fluorobenzyl)-1'-piperazinyl]-1-propanone dihydrochloride: The solid formed was converted to its free base using NH$_4$OH, extracted with dichloromethane and purified via flash chromatography (Silica, EtOAc). The resulting compound was converted to its dihydrochloride salt by the addition of dry ether-HCl to give the desired product: mp 213–216° C.; $^1$H NMR of the free base (300 MHz, CDCl$_3$) δ 7.83 (t, 1 H), 7.5 (m, 1 H), 7.4–6.95 (m, 6 H), 3.6 (s, 2 H), 3.2 (m, 2 H), 2.8 (t, 2 H), 2.5 (brs, 8 H).

EXAMPLE 31

1-(m-Nitrophenyl)-3-[4'-(o-fluorobenzyl)-1'-piperazinyl]-1-propanone dihydrochloride: $^1$H NMR of the free base (300 MHz, CDCl$_3$) δ 8.78 (s, 1 H), 8.42 (d, 1 H), 8.28 (d, 1 H), 7.7 (t, 1 H), 7.37 (t, 1 H), 7.24 (m, 1 H), 7.15–6.95 (m, 2 H), 3.6 (s, 2 H), 3.22 (t, 2 H), 2.88 (t, 2 H), 2.56 (brs, 8 H).

EXAMPLE 32

1-(p-Nitrophenyl)-3-[4'-(o-fluorobenzyl)-1'-piperazinyl]-1-propanone dihydrochloride: The solid formed was converted to its free base using NH$_4$OH, extracted with dichloromethane and purified via flash chromatography (Silica, 9:1 EtOAc/MeOH). The resulting compound was converted back to its dihydrochloride salt by the addition of dry ether-HCl and recrystallized from methanol (2x) to give the desired product: $^1$H NMR of the free base (300 MHz, CDCl$_3$) δ 8.3 (d, 2 H), 8.1 (d, 2 H), 7.9–6.95 (m, 4 H), 3.6 (s, 2 H), 3.2 (t, 2 H), 2.85 (t, 2 H), 2.5 (brs, 8 H).

EXAMPLE 33

1-(p-Nitrophenyl)-3-[4'-(2",5"-difluorobenzyl)-1'-piperazinyl]-1-propanone dihydrochloride: The solid was basified with NH$_4$OH, extracted with dichloromethane, purified via flash chromatography (Silica, EtOAc), and converted to the dihydrochloride salt by the addition of dry ether-HCl. This was recrystallized in methanol (2x) to give the desired product. mp 212–215° C.; $^1$H NMR of the free base (300 MHz, CDCl$_3$) δ 8.3 (d, 2 H), 8.1 (d, 2 H), 7.2–6.8 (m, 3 H), 3.55 (s, 2 H), 3.2 (t, 2 H), 2.85 (t, 2 H), 2.55 (brs, 8 H).

EXAMPLE 34

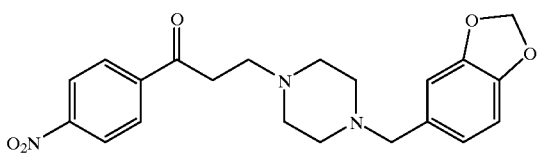

1-(p-Nitrophenyl)-3-(4'-piperonyl-1'-piperazinyl)-1-propanone dihydrochloride: The solid was basified with NH$_4$OH, extracted with dichloromethane and purified via flash chromatography (Silica, EtOAc). The resulting compound was converted to the dihydrochloride salt by the addition of dry ether-HCl and recrystallized in methanol to give the desired product: mp 214–217° C.; $^1$H NMR of the free base (300 MHz, CDCl$_3$) δ 8.3 (d, 2 H), 8.1 (d, 2 H), 6.9–6.65 (m, 3 H), 5.95 (s, 2 H), 3.4 (s, 2 H), 3.21 (t, 2 H), 2.83 (t, 2 H), 2.5 (brm, 8 H).

EXAMPLE 35

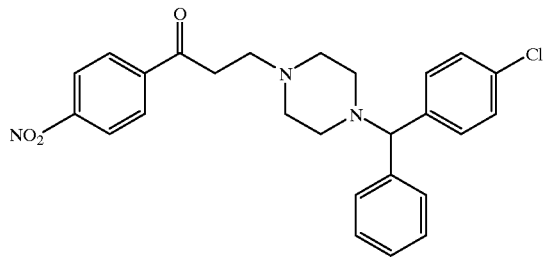

1-(p-Nitrophenyl)-3-[4'-(1"-p-chlorophenyl-1"-phenylmethyl)-1'-piperazinyl]-1-propanone dihydrochloride: The reaction was concentrated in vacuo, basified with NH$_4$OH, extracted with dichloromethane and purified via flash chromatography (Silica, EtOAc). The resulting compound was converted to its dihydrochloride salt by the addition of dry ether-HCl to give the desired product: mp 148–153° C.; $^1$H NMR of the free base (300 MHz, CDCl$_3$) δ 8.3 (d, 2 H), 8.1 (d, 2 H), 7.45–7.1 (m, 9 H), 4.2 (s, 1 H), 3.2 (t, 2 H), 2.85 (t, 2 H), 2.7–2.3 (brm, 8 H).

EXAMPLE 36

1-(p-Methanesulfonamidophenyl)-3-[(2",5"-difluorobenzyl)-1'-piperazinyl]-1-propanone dihydrochloride: mp 230–232° C.; $^1$H NMR (300 MHz, D$_2$O) δ 7.88 (d, 2 H), 7.3–7.05 (m, 5 H), 4.28 (s, 2 H), 3.8–3.3 (brm, 12 H), 3.06 (s, 3 H).

EXAMPLE 37

1-(3"-Thienyl)-3-[4"-(m-fluorobenzyl)-1'-piperazinyl]-1-propanone dihydrochloride: The solid was basified with NH$_4$OH, extracted with dichloromethane and purified via flash chromatography (Silica, EtOAc). The free amine was converted to its dihydrochloride salt by the addition of dry ether-HCl to give the desired product: $^1$H NMR of the free base (300 MHz, CDCl$_3$) δ 8.06 (d, 1 H), 7.53 (d, 1 H), 7.29 (m, 2 H), 7.08 (m, 2 H), 6.93 (m, 1 H), 3.5 (s, 2 H), 3.12 (t, 2 H), 2.85 (t, 2 H), 2.54 (brm, 8 H).

EXAMPLE 38

1-(3"-Thienyl)-3-[4'-(2'",5'"-difluorobenzyl)-1'-piperazinyl]-1-propanone dihydrochloride: $^1$H NMR of the free base (300 MHz, CDCl$_3$) δ 8.05 (d, 1 H), 7.54 (d, 1 H), 7.32 (m, 1 H), 7.12 (m, 1 H), 6.94 (m, 2 H), 3.57 (s, 2 H), 3.1 (t, 2 H), 2.83 (t, 2 H), 2.56 (brs, 8 H).

EXAMPLE 39

1-(p-Nitrophenyl)-3-([4'-(o-trifluoromethyl)benzoyl]-1'-piperazinyl)-1-propanone: The solid was basified with NH$_4$OH, extracted with dichloromethane and purified via flash chromatography (Silica, EtOAc) to give the desired product: mp 179–181° C.; $^1$H NMR (300 MHz, CDCl$_3$) δ 8.32 (d, 2 H), 8.1 (d, 2 H), 7.72 (d, 1 H), 7.56 (m, 2 H), 7.33 (d, 1 H), 3.82 (m, 2 H), 3.2 (m, 4 H), 2.88 (t, 2 H), 2.6 (m, 2 H), 2.62, (m, 2 H).

EXAMPLE 40

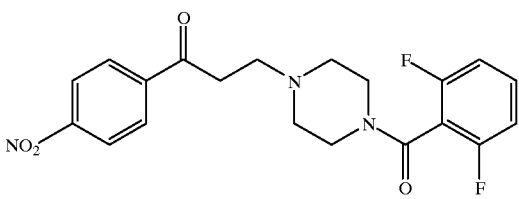

1-(p-Nitrophenyl)-3-[4'-(2",6"-difluorobenzoyl)-1'-piperazinyl]-1-propanone hydrochloride: mp 225–227° C.; $^1$H NMR (300 MHz, D$_2$O/CD$_3$OD) δ 8.21 (d, 2 H), 8.03 (d, 2 H), 7.42 (m, 1 H), 6.98 (t, 2 H), 3.78–3.15 (brm, 12 H).

EXAMPLE 41

1-(o-Fluorophenyl)-3-[4'-(2",6"-difluorobenzoyl)1'-piperazinyl]-1-propanone hydrochloride: mp 185–187° C.; $^1$H NMR (300 MHz, CDCl$_3$) δ 13.55–13.73 (brs, 1 H), 7.87–7.65 (m, 1 H), 7.65–7.35 (m, 2 H), 7.35–6.90 (m, 4 H), 2.92 (d, 1 H), 4.15 (t, 1 H), 3.90–3.40 (m, 8 H), 3.05–2.80 (m, 2 H).

EXAMPLE 42

1-(p-Nitrophenyl)-3-[4'-(m-fluorobenzyl)-1'-piperazinyl]-1-propanone dihydrochloride: mp 210° C. (dec.); $^1$H NMR (300 MHz, DMSO-d$_6$) δ 12.10–11.30 (brs, 2 H), 8.40 (d, 2 H), 8.25 (d, 2 H), 7.60–7.20 (m, 4 H), 4.45–3.00 (m, 14 H).

EXAMPLE 43

1-(o-Fluorophenyl)-3-[4'-(o-trifluoromethylbenzoyl)-1'-piperazinyl]-1-propanone hydrochloride: mp 175–176° C.; $^1$H NMR (300 MHz, CDCl$_3$) δ 13.55–13.45 (brs, 1 H), 7.98–7.50 (m, 5 H), 7.45–7.10 (m, 3 H), 4.92 (d, 1 H), 4.12 (t, 1 H), 3.95–3.35 (m, 8 H), 3.10–2.70 (m, 2 H).

EXAMPLE 44

1-(o-Fluorophenyl)-3-[4'-(p-fluorobenzyl)-1'-piperazinyl]-1-propanone dihydrochloride: mp 209° C. (dec.); $^1$H NMR (300 MHz, DMSO-d$_6$) δ 12.00–11.40 (brs, 2 H), 7.95–7.20 (m, 8 H), 4.30 (s, 2 H), 3.85–3.20 (m, 12 H).

EXAMPLE 45

1-(p-Nitrophenyl)-3-[4'-(p-fluorobenzyl)-1'-piperazinyl]-1-propanone dihydrochloride: mp 200° C. (dec.); $^1$H NMR (300 MHz, DMSO-d$_6$) δ 12.50–11.60 (brs, 2 H), 8.50 (d, 2 H), 8.25 (d, 2 H), 7.85–7.20 (m, 4 H), 4.39 (s, 2 H), 4.00–3.00 (m, 12 H).

EXAMPLE 46

1-(p-Fluorophenyl)-3-[4'-(p-fluorobenzyl)-1'-piperazinyl]-1-propanone dihydrochloride: mp 224° C. (dec.); $^1$H NMR (300 MHz, DMSO-d$_6$) δ 12.40–11.70 (brs, 2 H), 8.05–7.20 (m, 8 H), 4.35 (brs, 2 H), 3.95–3.10 (m, 12 H).

EXAMPLE 47

1-(m-Fluorophenyl)-3-[4'-(p-fluorobenzyl)-1'-piperazinyl]-1-propanone dihydrochloride: mp 215° C. (dec.); $^1$H NMR (300 MHz, DMSO-d$_6$) δ 12.05–11.75 (brs, 2 H), 7.95–7.15 (m, 8 H), 4.35 (brs, 2 H), 3.95–3.15 (m, 12 H).

EXAMPLE 48

1-(p-Iodophenyl)-3-[4'-p-fluorobenzyl)-1'-piperazinyl]-1-propanone dihydrochloride: mp 215° C. (dec.); $^1$H NMR (300 MHz, DMSO-d$_6$) δ 12.25–11.70 (brs, 2 H), 7.95 (d, 2 H), 7.80–7.50 (m, 4 H), 7.40–7.20 (m, 2 H), 4.30 (s, 2 H), 3.90–3.10 (m, 12 H).

EXAMPLE 49

(a) 4-Fluorobenzoylpiperazine: p-Fluorobenzoylchloride (6.00 g) in 30 mL CH$_3$CN was added in one portion to a stirred solution of piperazine (16.25 g) dissolved in 1N HCl (285 mL). The reaction was stirred at room temperature for 3.5 hrs. then an additional 50 mL of 1N HCl was added. The solution was extracted with 2×100 mL EtOAc. The aqueous acidic layer was made basic with 1N KOH then extracted with 2×150 mL CH$_2$Cl$_2$. The organic layer was separated, dried (Na$_2$SO$_4$), filtered and evaporated, affording a yellow oil which solidified upon standing (5.60 g; 71% yield). M$^+$ 208. $^1$H NMR (300 MHz, CDCl$_3$) δ 7.50–7.35 (m, 2 H), 7.18–7.00 (m, 2 H), 3.90–3.30 (brd, 4 H), 3.00–2.70 (brs, 4 H), 1.85 (s, 1 H).

(b) 3-Fluorobenzoylpiperazine: Utilizing the procedure of Example 49a but replacing p-fluorobenzoylchloride with m-fluorobenzoylchloride (3.00 g) afforded the desired product (3.20 g; 82% yield). M$^+$ 208. $^1$H NMR (300 MHz, CDCl$_3$) δ 8.50–7.32 (m, 1 H), 7.25–7.05 (m, 3 H), 3.75 (brs, 2 H), 3.40 (brs, 2 H), 3.05–2.65 (m, 4 H), 1.90 (s, 1 H).

(c) 2-Fluorobenzoylpiperazine: Using the procedure of Example 49a and o-fluorobenzoylchloride (2.00 g) gave the desired product (2.40 g; 90% yield). M$^+$ 208. $^1$H NMR (300 MHz, CDCl$_3$) δ 7.50–7.00 (m, 4 H), 2.90–3.70 (m, 2 H), 3.45 (brs, 2 H), 3.10–2.65 (m, 4 H), 1.85 (s, 1 H).

(d) 2,5-Difluorobenzoylpiperazine: Using the procedure of Example 49a with 2,5-difluorobenzoylchloride (5.00 g) gave the desired product (3.00 g; 51% yield). M$^+$ 226. $^1$H NMR (300 MHz, CDCl$_3$) δ 7.20–7.00 (m, 3 H), 3.86–3.70 (m, 2 H), 3.40–3.25 (m, 2 H), 3.05–2.75 (m, 4 H), 1.97 (s, 1 H).

(e) 4-Trifluoromethylbenzoylpiperazine: Using the procedure of Example 49a with p-trifluoromethylbenzoylchloride (5.00 g) gave the desired product (1.85 g; 30% yield). M$^+$ 258. $^1$H NMR (300 MHz, CDCl$_3$) δ 7.67 (d, 2 H), 7.50 (d, 2 H), 3.75 (brs, 2 H), 3.35 (brs, 2 H), 3.05–2.75 (m, 2 H), 1.85 (s, 1 H).

(f) 2,3-Difluorobenzoylpiperazine: Using the procedure of Example 49a with 2,3-difluorobenzoylchloride (5.00 g) gave the desired product (3.00 g; 47% yield). M$^+$ 226. $^1$H NMR (300 MHz, CDCl$_3$) δ 7.35–7.05 (m, 3 H), 3.75 (brs, 2 H), 3.30 (brs, 2 H), 3.06–2.75 (m, 4 H), 1.75 (s, 1 H).

(g) 2-Trifluoromethylbenzoylpiperazine: Using the procedure of Example 49a with o-trifluoromethylbenzoylchloride (5.00 g) gave the desired product (3.4 g; 55% yield). M$^+$ 258. $^1$H NMR (300 MHz, CDCl$_3$) δ 795–7.45 (m, 3 H), 7.40–7.25 (m, 1 H), 3.90–3.70 (m, 2 H), 3.25–3.05 (m, 2 H), 3.00–2.85 (m, 2 H), 2.85–2.65 (m, 2 H), 1.70 (s, 1 H).

(h) 4-Nitrobenzoylpiperazine: Using the procedure of Example 49a with p-nitrobenzoylchloride (7.00 g) gave the desired product (4.50 g; 50% yield). M$^+$ 235. $^1$H NMR (300 MHz, CDCl$_3$) δ 8.27 (d, 2 H), 7.07 (d, 2 H), 3.90–3.60 (brs, 2 H), 3.45–3.25 (brs, 2 H), 3.10–2.70 (m, 4 H), 1.75 (s, 1 H).

(i) 2,6-Difluorobenzoylpiperazine: Using the procedure of Example 49a with 2,6-difluorobenzoylchloride (5.00 g) gave the desired product (3.25 g; 51% yield). M$^+$ 226. $^1$H NMR (300 MHz, CDCl$_3$) δ 7.45–7.25 (m, 1 H), 7.05–6.85 (m, 2 H), 3.70–3.40 (brs, 2 H), 3.40–3.25 (brs, 2 H), 3.05–2.75 (m, 4 H), 1.70 (s, 1 H).

(j) 4-Iodobenzoylpiperazine: Using the procedure of Example 49a with 4-iodobenzoylchloride (4.24 g) gave the desired product (0.70 g; 14% yield). M$^+$–316. $^1$H NMR (300 MHz, CDCl$_3$) δ 7.85–7.15 (d, 2 H), 7.20–7.05 (d, 2 H), 3.85–3.05 (brs, 2 H), 3.55–3.25 (brs, 2 H), 3.10–2.65 (m, 4 H), 1.75 (s, 1 H).

(k) 4-Methanesulphonamido acetophenone: A $CH_2Cl_2$ (130 mL) solution containing 4-aminoacetophenone (5.00 g) and triethylamine (5.6 mL) was cooled to 0° C. and placed under nitrogen. Then, methanesulfonylchloride (3.1 mL) in $CH_2Cl_2$ (5 mL) was added dropwise over 10 min. Upon complete addition the reaction was stirred at 0° C. for an additional 10 min. then allowed to warm to room temperature with stirring continuing for 2 hrs. Then 1N KOH was added and the layers separated. The basic layer was made acidic, then extracted with $CH_2Cl_2$ (2×75 mL). The organic extracts were combined, dried ($Na_2SO_4$), filtered and evaporated affording a pale yellow solid (4.10 g; 52% yield). $M^+$ 213. $^1H$ NMR (300 MHz, $CDCl_3$) δ 7.97 (d, 2 H), 7.27 (d, 2 H), 3.10 (s, 3 H), 2.07 (s, 3 H).

(l) 3-Methanesulphonamido acetophenone: Using the procedure of Example 49k but starting with 3-aminoacetophenone (5.00 g) gave the desired product (6.00 g; 76% yield). $M^+$ 213. $^1H$ NMR (300 MHz, $CDCl_3$) δ 7.92–7.45 (m, 5 H), 3.52 (s, 3 H), 2.65 (s, 3 H).

(m) 2-Fluorobenzylpiperazine: The product from Example 49c (3.10 g) was dissolved in dry THF (75 mL) then a 1M $B_2H_6$THF solution (45 mL) was added dropwise over ca. 15 min. under $N_2$. Upon complete addition, the solution was refluxed under $N_2$ for 3 hrs. The reaction was cooled to 0° C. in an ice bath and then 1N HCl (ca 70 mL) was carefully added dropwise. Upon complete addition, the reaction was allowed to warm to room temperature followed by extraction with EtOAc (2×100 mL). The organic layer was discarded and the acidic layer made basic with KOH. This was extracted with $CH_2Cl_2$ (2×150 mL). The organic extracts were combined, dried ($Na_2SO_4$), filtered and evaporated giving an oil that began to solidify upon standing. This was dissolved in 1N HCl (75 mL) then refluxed 1.5 hrs. The reaction was cooled to 0° C. then made basic with KOH followed by $CH_2Cl_2$ extraction (2×100 mL). The organic extracts were combined, dried ($Na_2SO_4$), filtered and evaporated affording a pale yellow oil (1.2 g; 41% yield). $M^+$ 194. $^1H$ NMR of the dihydrochloride salt (300 MHz, $CDCl_3$) δ 10.00–9.30 (brs, 2 H), 7.15–6.85 (m, 4 H), 3.62 (s, 2 H), 3.35–3.15 (m, 2 H), 2.90–2.70 (m, 2 H).

(n) 2,3-Difluorobenzylpiperazine: Using the product from Example 49f (1.14 g) and the procedure of Example 49m gave the desired product (0.45 g; 43% yield). $M^+$ 212. $^1H$ NMR (300 MHz, $CDCl_3$) δ 7.20–6.97 (m, 2 H), 3.60 (s, 2 H), 2.90 (t, 4 H), 2.55–2.35 (brs, 4 H), 1.67 (s, 1 H).

(o) 4-Nitrobenzylpiperazine: Using the product from Example 49h (0.50 g) and the procedure of Example 49m gave the desired product (0.28 g; 59% yield). $M^+$ 221. $^1H$ NMR (300 MHz, $CDCl_3$) δ 8.27 (d, 2 H), 7.15 (d, 2 H), 3.75 (s, 2 H), 3.30–3.15 (m, 4 H), 2.85–2.70 (m, 4 H).

(p) 2,5-Difluorobenzylpiperazine: Using the compound of Example 49d (2.90 g) and the procedure of Example 49m gave the desired product (2.30 g; 83% yield). $M^+$ 212. $^1H$ NMR (300 MHz, $CDCl_3$) δ 7.36–7.22 (m, 1 H), 7.10–6.90 (m, 3 H), 3.55 (s, 2 H), 3.30–3.10 9m, 4 H), 2.85–2.65 (m, 4 H).

(q) 4-Fluorobenzylpiperazine: Using the compound of Example 49a (5.25 g) and the procedure of Example 49m gave the desired product (4.35 g, 75% yield). $M^+$ 194. 1H NMR (300 MHz, $CDCl_3$) δ 8.95–8.70 (brs, 1 H), 7.40–7.25 (m, 2 H), 7.25–7.05 (m, 2 H), 3.50 (s, 2 H), 3.15–2.95 (brs, 2 H), 2.65–2.35 (m, 2 H).

(r) 1-Benzensulfonylpiperazine: Benzenesulfonyl chloride (2.00 g, 0.011 mol) in 25 mL $CH_3CN$ was added in one portion to a stirred solution of piperazine (4.90 g, 0.057 mol) dissolved in 1N HCl (100 mL). The reaction was stirred at room temperature for 30 minutes. The solution was extracted with EtOAc and the aqueous acid layer was made basic with 1N KOH and then extracted with 2×10 mL $CH_2Cl_2$. The organic layer was separated, dried ($MgSO_4$), filtered, and evaporated affording 1.40 g (50%) of a pale yellow solid: mp 109–111° C.; $^1H$ NMR (300 MHz, $CDCl_3$) δ 7.75 (m, 2 H), 7.65–7.40 (m, 3 H), 2.96 (m, 8 H).

(s) 1-(2'-Chloro-6'-methylpyrido-4'-yl)piperazine: 2-Chloro-6-methylpyridine-4-carbonyl chloride (5.00 g, 0.026 mol) in 50 mL $CH_3CN$ was added in one portion to a stirred solution of piperazine (11.31 g, 0.13 mol) dissolved in 1N HCl (180 mL). The reaction was stirred at room temperature for 3 hours, then an additional 50 mL of 1N HCl was added. The solution was extracted with EtOAc (2×150 mL), the aqueous acid layer was made basic with 1N KOH and then extracted with 2×10 mL $CH_2Cl_2$ (2×200 mL). The organic layer was separated, dried ($MgSO_4$), filtered and concentrated, affording 3.30 g (53%) of a light yellow solid: mp 164–165° C.; $^1H$ NMR (300 MHz, $CDCl_3$) δ 7.12 (s, 1 H), 7.06 (s, 1 H), 3.74 (m, 2 H), 3.33 (m, 2 H), 2.95 (m, 2 H), 2.83 (m, 2 H), 2.57 (s, 3 H), 1.72 (s, 1 H).

(t) p-Toluenesulfonylpiperazine: Using the procedure of Example 49r with p-toluenesulfonyl chloride gave the desired product: mp 98–101° C.; $^1H$ NMR (300 MHz, $CDCl_3$) δ 7.64 (d, 2 H), 7.34 (d, 2 H), 2.95 (m, 8 H), 2.44 (s, 3 H), 1.60 (brs, 1 H).

(u) p-Bromobenzenesulfonylpiperazine: Using the procedure of Example 49r p-bromobenzenesulfonyl chloride gave the desired product: mp 117–121° C.; $^1H$ NMR (300 MHz, $CDCl_3$) δ 7.66 (dd, 4 H), 2.97 (m, 8 H), 2.44 (s, 3 H), 1.60 (brs, 1 H).

EXAMPLES 50 AND 51

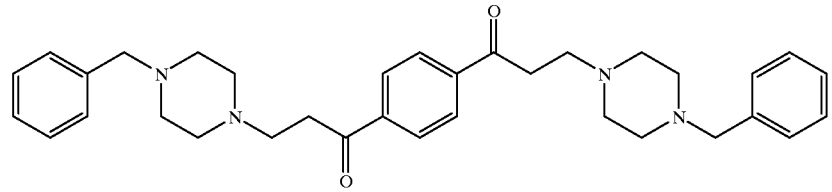

50

-continued

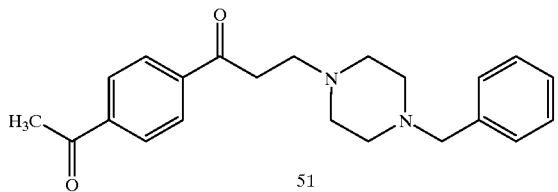

51

1,4-Bis-[3'-(4"-benzyl-1"-piperazinyl)-propanoyl]benzene (50) and 1-(p-Acetylphenyl)-3-(4'-benzyl-1'-piperazinyl)-1-propanone dihydrochloride (51): Using the general method gave both compounds after purification via flash chromatography (Silica, EtOAc). Each was converted to its dihydrochloride salts by the addition of dry ether-HCl. Higher $R_{f1}$=0.43 (8:2 EtOAc/MeOH) gave 8 mg (50): mp >250° C.; $^1$H NMR of the free base (300 MHz, CDCl$_3$) δ 8.0

1-(p-Nitrophenyl)-3-(4'-o-fluorobenzoyl-1'-piperazinyl)-1-propanone dihydrochloride: The solid was basified with NH$_4$OH, extracted with dichloromethane and purified via (s, 4 H), 7.3 (m, 5 H), 3.5 (s, 2 H), 3.2 (t, 2 H), 2.85 (t, 2 H), 2.65 (s, 3 H), 2.5 (brm, 8 H). Lower $R_{f2}$=0.14 (8:2 EtOAc/MeOH) gave 0.21 g (51): mp >245° C.; $^1$H NMR of the free base (300 MHz, CDCl$_3$) δ 8.0 (s, 4 H), 7.3 (m, 10 H), 3.5 (s, 4 H), 3.2 (t, 4 H), 2.85 (t, 4 H), 2.5 (brm, 16 H).

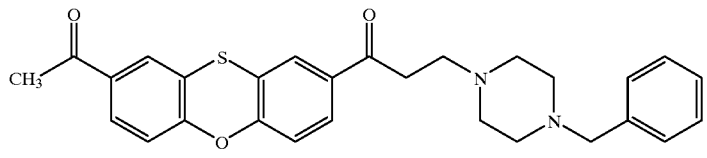

52

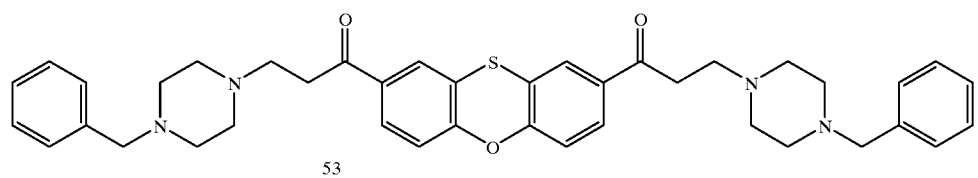

53

1-(8"-Acetylphenoxathiin-2"-yl)-3-(4'-benzyl-1'-piperazinyl)-1-propanone dihydrochloride (52) and 2,8-Bis-[3'(4"-benzyl-1"-piperazinzyl)propanoyl]phenoxathiin (53): According to Examples 50 and 51, 1,4-diacetylbenzene was replaced with 2,8-diacetylphenoxathiin (0.25 g, 0.88 mmol). After purification by flash chromatography (Silica, EtOAc) the two products were isolated $R_{f1}$=0.47 (8:2 EtOAc/MeOH) was converted to its corresponding salt by the addition of dry ether-HCl to give 95 mg (52): mp >250° C.; $^1$H NMR of the free base (300 MHz, CDCl$_3$) δ 7.8–7.5 (m, 4 H), 7.3 (m, 5 H), 7.15–6.95 (m, 2 H), 3.5 (s, 2 H), 3.1 (m, 2 H), 2.8 (m, 2 H), 2.65–2.3 (brm, 11 H). $R_{f2}$=0.24 (8:2 EtOAc/MeOH) was converted to its corresponding hydrochloride salt to give 35 mg (53): mp >250° C.; $^1$H NMR of the free base (300 MHz, CDCl$_3$) δ 7.8–7.5 (m, 4 H), 7.3 (m, 10 H), 7.15 (d, 1 H), 7.05 (d, 1 H), 3.55 (s, 4 H), 3.1 (m, 4 H), 2.85 (m, 4 H), 2.5 (brm, 16 H).

EXAMPLE 54

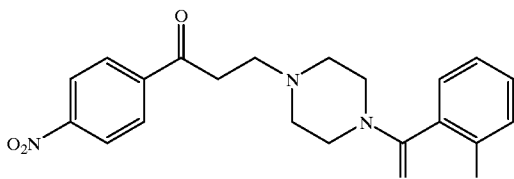

EXAMPLES 52 AND 53 flash chromatography (Silica, EtOAc). The free amine was converted to its hydrochloride salt by the addition of dry ether-HCl; filtered and dried: mp 217–218° C.; $^1$H NMR of the free base (300 MHz, CDCl$_3$) δ 8.32 (d, 2 H), 8.11 (d, 2 H), 7.4 (m, 2 H), 7.27–6.99 (m, 2 H), 3.8 (m, 2 H), 3.48–3.1 (m, 4 H), 2.89 (t, 2 H), 2.7–2.35 (m, 4 H).

EXAMPLE 55

1-(p-Nitrophenyl)-3-[4'-(3",4"-difluorobenzyl)-1'-piperazinyl]-1-propanone dihydrochloride: mp 210–212° C.; $^1$H NMR (300 MHz, D$_2$O) δ 8.22 (d, 2 H), 8.04 (d, 2 H), 7.37–7.09 (m, 3 H), 4.35 (s, 2 H), 3.7–3.35 (brm, 12 H).

EXAMPLE 56

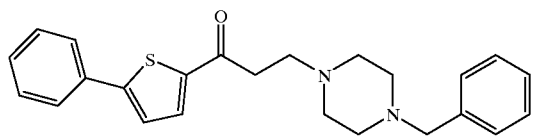

1-(5"-Phenyl-2"-thienyl)-3-(4'-benzyl-1'-piperazinyl)-1-propanone dihydrochloride: mp 224–247° C.; $^1$H NMR (300 MHz, D$_2$O) δ 7.76 (m, 1 H), 7.67 (m, 2 H), 7.37 (m, 9 H), 4.33 (s, 2 H), 3.5 (brm, 12 H).

EXAMPLE 57

1-(5"-Bromo-2"-thienyl)-3-(4'-benzyl-1'-piperazinyl)-1-propanone dihydrochloride: The solid was basified with NH$_4$OH, extracted with dichloromethane and purified via flash chromatography (Silica, EtOAc). The free amine was converted to its hydrochloride salt by the addition of dry ether-HCl; filtered and dried: mp 242–244° C.; $^1$H NMR (300 MHz, D$_2$O) δ 7.58 (d, 1 H), 7.37 (brs, 5 H), 7.15 (d, 1 H), 4.32 (s, 2 H), 3.5 (brm, 12 H).

EXAMPLE 58

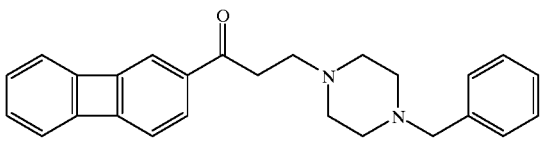

1-(Biphenylen-2"-yl)-3-(4'-benzyl-1'-piperazinyl)-1-propanone: mp 133–134° C.; $^1$H NMR (300 MHz, CDCl$_3$) δ 7.46 (d, 1 H), 7.29 (m, 5 H), 7.17 (s, 1 H), 6.9–6.65 (brm, 5 H), 3.52 (s, 2 H), 3.04 (t, 2 H), 2.81 (t, 2 H), 2.52 (brs, 8 H).

EXAMPLE 59

1-(5"-Chloro-2"-thienyl)-3-(4'-benzyl-1'-piperazinyl)-1-propanone dihydrochloride: mp 248–249° C.; $^1$H NMR (300 MHz, D$_2$O) δ 7.63 (d, 1 H), 7.36 (brs, 5 H), 7.0 (d, 1 H), 4.28 (s, 2 H), 3.44 (brm, 12 H).

EXAMPLE 60

1-(m-Cyanophenyl)-3-(4'-benzyl-1'-piperazinyl)-1-propanone dihydrochloride: The solid was basified with NH$_4$OH, extracted with dichloromethane and purified via flash chromatography (Silica, EtOAc). The free amine was converted to its hydrochloride salt by the addition of dry ether-HCl; filtered and dried: mp 247–248° C.; $^1$H NMR (300 MHz, CDCl$_3$) δ 8.28–8.1 (m, 2 H), 7.84 (d, 1 H), 7.61 (t, 1 H), 7.3 (brm, 5 H), 3.51 (s, 2 H), 3.17 (t, 2 H), 2.84 (t, 2 H), 2.5 (brm, 8 H).

EXAMPLE 61

1-(6"-Fluoro-2"-methylphenyl)-3-(4'-benzyl-1'-piperazinyl)-1-propanone dihydrochloride: mp 210° C. (dec.); $^1$H NMR (300 MHz, DMSO-d$_6$) δ 12.15–11.40 brs, 2 H), 8.05–7.95 (m, 1 H), 7.70–7.40 (m, 5 H), 7.30–7.20 (m, 2 H), 4.55–4.20 (brs, 2 H), 3.90–3.20 (m, 12 H).

EXAMPLE 62

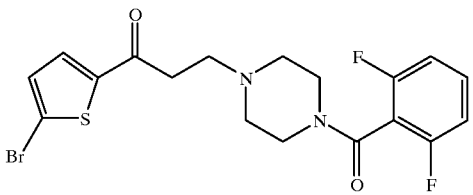

1-(5'"-Bromo-2'"-thienyl)-3-[4'-(2",6"-difluorobenzoyl)-1'-piperazinyl]-1-propanone hydrochloride: mp 225–226° C.; $^1$H NMR (300 MHz, DMSO-d$_6$/D$_2$O) δ 7.9 (d, 1 H), 7.63 (m, 1 H), 7.49 (d, 1 H), 7.28 (t, 2 H), 4.65 (brs, 2 H), 3.95–3.03 (m, 12 H).

EXAMPLE 63

1-(p-Nitrophenyl)-3-[4'-(2",3"-difluorobenzoyl)-1'-piperazinyl]-1-propanone dihydrochloride: The solid was basified with NH$_4$OH, extracted with dichloromethane and purified via flash chromatography (Silica, EtOAc). The free amine was converted to its hydrochloride salt by the addition of dry ether-HCl; filtered and dried: mp 213–214° C.; $^1$H NMR (300 MHz, DMSO-d$_6$) δ 10.7 (brs, 1 H), 8.39 (d, 2 H), 8.23 (d, 2 H), 7.58 (m, 1 H), 7.34 (m, 2 H), 3.85–3.0 (m, 12 H).

EXAMPLE 64

1-(o-Chlorophenyl)-3-(4'-benzyl-1'-piperazinyl)-1-propanone dihydrochloride: The solid was basified with NH$_4$OH, extracted with dichloromethane and purified via flash chromatography (Silica, EtOAc). The free amine was converted to its dihydrochloride salt by the addition of dry ether-HCl; filtered and dried: mp >250° C.; $^1$H NMR (300 MHz, D$_2$O) δ 7.8–7.18 (m, 9 H), 4.55 (s, 2 H), 3.64 (brs, 12 H).

EXAMPLE 65

1-(o-Nitrophenyl)-3-(4'-benzyl-1'-piperazinyl)-1-propanone dihydrochloride: The solid was basified with NH$_4$OH, extracted with dichloromethane and purified via flash chromatography (Silica, EtOAc). The free amine was converted to its dihydrochloride salt by the addition of dry ether-HCl; filtered and dried: mp 226–228° C.; $^1$H NMR (300 MHz, D$_2$O) δ 8.25 (d, 1 H), 7.89 (t, 1 H), 7.79 (t, 1 H), 7.56 (m, 6 H), 4.4 (s, 2 H), 3.7–3.28 (brm, 12 H).

EXAMPLE 66

1-(o-Bromophenyl)-3-(4'-benzyl-1'-piperazinyl)-1-propanone dihydrochloride: mp >250° C.; $^1$H NMR (300 MHz, DMSO-d$_6$, H$_2$O) δ 7.73 (d, 2 H), 7.64–7.3 (m, 7 H), 4.25 (brm, 2 H), 3.52 (brs, 12 H).

EXAMPLE 67

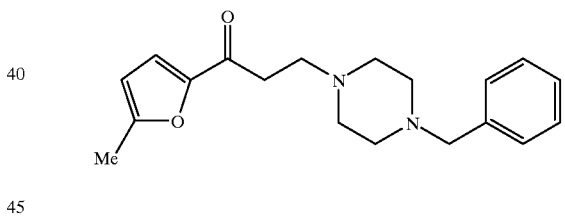

1-(5"-Methyl-2"-furanyl)-3-(4'-benzyl-1'-piperazinyl)-1-propanone hydrochloride: mp 213° C. (dec.); $^1$H NMR (300 MHz, DMSO-d$_6$) δ 12.40–11.60 (brs, 2 H), 7.75–7.55 (brs, 2 H), 7.55–7.35 (brs, 4 H), 6.4 (d, 1 H), 4.55–4.20 (brs, 2 H), 3.80–3.20 (m, 12 H), 2.35 (s, 3 H), 3.90–3.30 (m, 20 H).

EXAMPLE 68

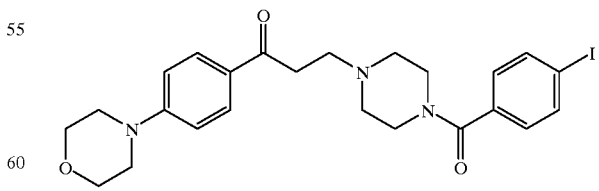

1-(p-N-Morpholinophenyl)-3-[4'-p-iodobenzoyl)-1'-piperazinyl]-1-propanone dihydrochloride: mp 240° C.; $^1$H NMR (300 MHz, CDCl$_3$) δ 7.91 (d, 2 H), 7.80 (d, 2 H), 7.17 (d, 2 H), 6.85 (d, 2 H).

EXAMPLE 69

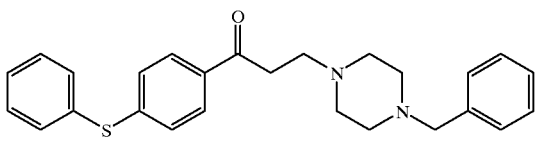

1-p-Phenylthiophenyl-3-(4'-benzyl-1'-piperazinyl)-3-propanone dihydrochloride: mp 210° C. (dec.); $^1$H NMR (300 MHz, DMSO-d$_6$) δ 12.30–11.10 (brs, 2 H), 7.90 (d, 2 H), 7.70–7.40 (m, 10 H), 7.30 (d, 2 H), 4.60–3.90 (brs, 2 H), 3.90–3.10 (m, 12 H).

EXAMPLE 70

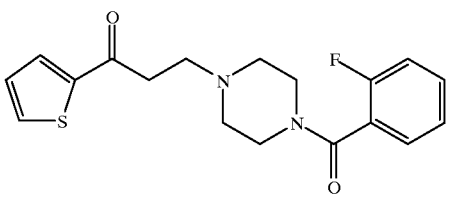

1-(2"-Thienyl)-3-[4'-(o-fluorobenzoyl)-1'-piperazinyl]-1-propanone hydrochloride: mp 183–184° C.; $^1$H NMR (300 MHz, CDCl$_3$) δ 10.30–10.07 (brs, 1 H), 7.90 (d, 1 H), 7.76 (d, 1 H), 7.55–7.35 (m, 2 H), 7.30–7.05 (m, 3 H), 4.97–4.80 (brd, 1 H), 4.15–3.95 (m, 1 H), 3.90–3.40 (m, 8 H), 3.05–2.8 (m, 2 H).

EXAMPLE 71

1-[4'-(p-Hydroxy-m-nitrophenyl)]-3-(4'-benzyl-1'-piperazinyl)-1-propanone dihydrochloride: mp 209–212° C.; $^1$H NMR (300 MHz, D$_2$O) δ 8.75 (s, 1 H), 8.24 (d, 1 H), 7.65–7.50 (brs, 5 H), 7.31 (d, 1 H), 4.51 (s, 2 H), 3.86–3.60 (m, 12 H).

EXAMPLE 72

1-(p-N-Morpholinophenyl)-3-(4'-benzyl-1'-piperazinyl)-1-propanone dihydrochloride: mp205° C. (dec.); $^1$H NMR (300 MHz, D$_2$O) δ 7.80 (d, 2 H), 7.45–7.30 (brs, 5 H), 6.95 (d, 2 H), 4.32 (s, 2 H), 3.80–3.66 (m, 4 H), 3.60–3.40 (m, 12 H), 3.30–3.20 (m, 4 H).

EXAMPLE 73

1-(p-Cyanophenyl)-3-(4'-benzyl-1'-piperazinyl)-1-propanone dihydrochloride: mp 190° C. (dec.); $^1$H NMR (300 MHz, DMS-d$_6$) δ 8.29–7.90 (m, 4 H), 7.70–7.15 (m, 5 H), 4.45–4.05 (brs, 2 H), 4.00–3.00 (m, 12 H).

EXAMPLE 74

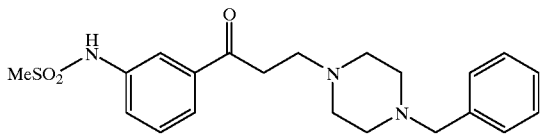

1-(m-Methanesulfonamidophenyl)-3-(4'-benzyl-1'-piperazinyl)-1-propanone dihydrochloride: mp 180–182° C.; $^1$H NMR (300 MHz, D$_2$O) δ 7.95–7.85 (m, 2 H), 7.65–7.,50 (m, 7 H), 4.49 (s, 2 H), 3.85–3.60 (brs, 12 H), 3.14 (s, 3 H).

EXAMPLE 75

1-(m-Fluorophenyl)-3-(4'-benzyl-1'-piperazinyl)-1-propanone dihydrochloride: mp 251–253° C.; $^1$H NMR (300 MHz, DMSO-d$_6$) δ 12.2 (brm, 2 H), 7.9–7.3 (m, 9 H), 4.4 (s, 2 H), 4.0–3.18 (m, 12 H).

EXAMPLE 76

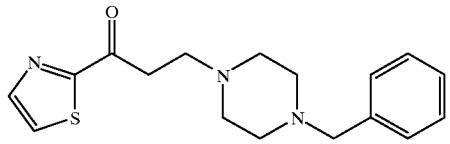

1-(2-Thiazolyl)-3-(4'-benzyl-1'-piperazinyl)-1-propanone dihydrochloride: The solid was basified with NH$_4$OH, extracted with dichloromethane and purified via flash chromatography (Silica, EtOAc): $^1$H NMR (300 MHz, CDCl$_3$) δ 8.0 (d, 1 H), 7.66 (d, 1 H), 7.28 (m, 5 H), 3.5 (s, 2 H), 3.37 (t, 2 H), 2.88 (t, 2 H), 2.5 (brm, 8 H).

EXAMPLE 77

1-[p-Trifluoromethyl]-phenyl]-3-(4'-benzyl-1'-piperazinyl)-1-propanone: The solid was basified with 1N KOH, extracted with dichloromethane, dried and filtered: mp 59–60° C.; $^1$H NMR (300 MHz, CDCl$_3$) δ 8.06 (d, 2 H), 7.74 (d, 2 H), 7.3 (m, 5 H), 3.52 (s, 2 H), 3.2 (t, 2 H), 2.87 (t, 2 H), 2.53 (brm, 8 H).

EXAMPLE 78

1-(5"-Bromo-2"-thienyl)-3-[4'-(1'''-p-chlorophenyl-1'''-phenylmethyl)-1'-piperazinyl]-1-propanone dihydrochloride: mp 141–144° C.; $^1$H NMR (300 MHz, CDCl$_3$) δ 7.44 (d, 1 H), 7.39–7.12 (m, 7 H), 7.07 (d, 1 H), 4.19 (s, 1 H), 3.10 (t, 2 H), 2.8 (t, 2 H), 2.65–2.25 (brm, 8 H).

EXAMPLE 79

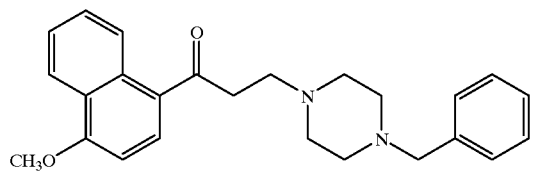

1-(4"-Methoxy-1"-naphthalenyl)-3-(4'-benzyl-1'-piperazinyl)-1-propanone dihydrochloride: mp 230° C. (dec.); $^1$H NMR (300 MHz, D$_2$O/DMSO-d$_6$) δ 8.88 (d, 1 H), 8.27 (t, 2 H), 7.73–7.35 (m, 7 H), 7.1 (d, 1 H), 4.52–4.02 (m, 5 H), 3.65 (brm, 12 H).

EXAMPLE 80

1-(5"-Nitro-3"-thienyl)-3-(4'-benzyl-1'-piperazinyl)-1-propanone dihydrochloride: mp 220° C. (dec.); $^1$H NMR (300 MHz, D$_2$O/DMSO-d$_6$) δ 88. (d, 1 H), 8.47 (d, 1 H), 7.66–7.42 (m, 5 H), 4.3 (s, 2 H), 3.85–3.2 (m, 12 H).

EXAMPLE 81

1-o-Iodophenyl-3-(4'-benzyl-1'-piperazinyl)-1-propanone dihydrochloride: mp 240–242° hu C.; $^1$H NMR of the free base (300 MHz, CDCl$_3$) δ 7.9 (d, 1 H), 7.5 (m, 8 H), 3.5 (s, 2 H), 3.08 (t, 2 H), 2.78 (t, 2 H), 2.49 (brs, 8 H).

EXAMPLE 82

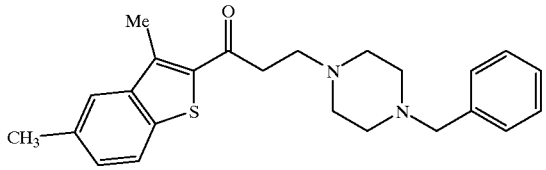

1-(5"-Chloro-3"-methylbenzo[b]-2"-thienyl)-3-(4'-benzyl-1'-piperazinyl)-1-propanone dihydrochloride: mp 247° C. (dec.); $^1$H NMR of the free base (300 MHz, CDCl$_3$) δ 7.84 (d, 1 H), 7.76 (d, 1 H), 7.45 (dd, 1 H), 73 (m, 5 H), 3.53 (s, 2 H), 3.15 (t, 2 H), 2.9 (t, 2 H), 2.71 (s, 3 H), 2.55 (brm, 8 H).

EXAMPLE 83

1-(5"-[2'"-Thienyl]-2"-thienyl)-3-(4'-benzyl-1'-piperazinyl)-1-propanone dihydrochloride: mp 249–252° C.; $^1$H NMR (300 MHz, D$_2$O/DMSO-d$_6$) δ 7.96 (d, 1 H), 7.67 (d, 1 H), 7.63–7.34 (m, 7 H), 7.15 (t, 1 H), 4.25 (brs, 2 H), 3.4 (brm, 12 H).

EXAMPLE 84

1-(5"-Bromo-2"-thienyl)-3-(4'-o-fluorobenzyl-1'-piperazinyl)-1-propanone dihydrochloride: mp 224–226° C.; $^1$H NMR of the free base (300 MHz, CDCl$_3$) δ 7.45 (d, 1 H), 7.36 (m, 1 H), 7.23 (m, 1 H), 7.15–6.92 (m, 3 H), 3.6 (s, 2 H), 3.03 (t, 2 H), 2.82 (t, 2 H), 2.54 (brs, 8 H).

EXAMPLE 85

1-(5"-Cyano-2"-thienyl)-3-(4'-benzyl-1'-piperazinyl)-1-propanone dihydrochloride: mp 256–258° C.; $^1$H NMR of the free base (300 MHz, CDCl$_3$) δ 7.63 (dd, 2 H), 7.27 (m, 5 H), 3.5 (s, 2 H), 3.1 (t, 2 H), 2.84 (t, 2 H), 2.5 (brm, 8 H).

EXAMPLE 86

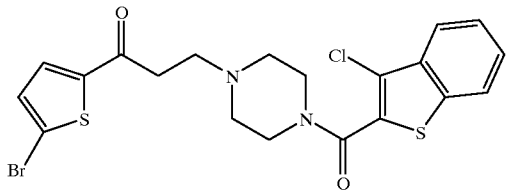

1-(5"-Bromo-2"-thienyl)-3-[4'-(3'"-chlorobenzo[b]-2'"-thienoyl)-1'-piperazinyl]-1-propanone dihydrochloride: mp 188–189° C.; $^1$H NMR of the free base (300 MHz, CDCl$_3$) δ 7.84 (m, 2 H), 7.48 (m, 3 H), 7.12 (d, 1 H), 3.83 (brm, 2 H), 3.5 (brm, 2 H), 3.04 (t, 2 H), 2.88 (t, 2 H), 2.58 (brs, 4 H).

EXAMPLE 87

1-(6"-Methoxy-2"-naphthalenyl)-3-(4'-benzyl-1'-piperazinyl)-1-propanone dihydrochloride: mp 243–246° C.; $^1$H NMR (300 MHz, D$_2$O/DMSO-d$_6$) δ 8.62 (s, 1 H), 8.12–7.86 (m, 3 H), 7.65–7.34 (m, 6 H), 7.27 (m, 1 H), 7.42–7.32 (m, 17 H).

EXAMPLE 88

1-(p-Methylthiophenyl)-3-(4'-(2",6"-difluorobenzyl)-1'-piperazinyl)-1-propanone dihydrochloride: mp 187–188° C.; $^1$H NMR (300 MHz, CDCl$_3$/MeOD) δ 7.90 (d, 2 H), 7.65–7.50 (m, 1 H), 7.30 (d, 2 H), 7.23–7.10 (m, 2 H), 4.00–3.40 (m, 14 H), 255 (s, 3 H).

EXAMPLE 89

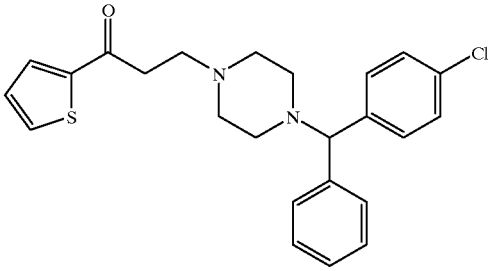

1-(2"-Thienyl)-3-[4'-(1'"-p-chlorophenyl-1'"-phenylmethyl)-1'-piperazinyl]-1-propanone dihydrochloride: mp 189–201° C.; $^1$H NMR (300 MHz, DMSO-d$_6$) δ 8.05 9d, 1 H), 8.00 (d, 1 H), 7.55–7.20 (m, 10 H), 4.60 (brs, 1 H), 3.80–3.20 (m, 12 H).

EXAMPLE 90

1-(-N-Piperidinophenyl)-3-(4'-benzyl-1'-piperazinyl)-1-propanone dihydrochloride: mp 135° C. (dec.); $^1$H NMR (300 MHz, CDCl$_3$/DMSO-d$_6$) δ 8.00 (d, 2 H), 7.90–7.40 (m, 7 H), 4.35 (s, 2 H), 4.15–5.00 (m, 2 H), 4.00–3.80 (m, 2 H), 3.80–3.40 (m, 12 H), 2.15–1.95 (m, 4 H), 1.80–1.65 (m, 2 H).

EXAMPLE 91

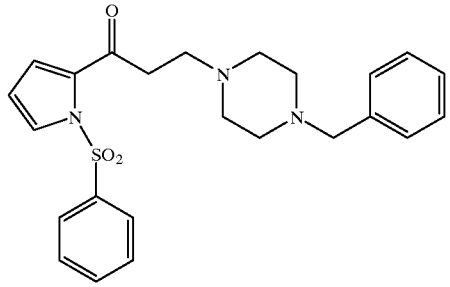

1-(N-Phenylsulfonylpyrrol-2-yl)-3-(4'-benzyl-1'-piperazinyl)-1-propanone dihydrochloride: mp 215° C. (dec.); $^1$H NMR (300 MHz, DMSO-d$_6$) δ 8.0807.85 (m, 2 H), 7.75–7.35 (m, 10 H), 6.60–6.50 (m, 1 H), 4.30 (brs, 2 H), 3.80–3.00 (m, 12 H).

EXAMPLE 92

1-[3',5'-Bis(trifluoroethoxy)phenyl]-3-(4'-benzyl-1'-piperazinyl)-1-propanone dihydrochloride: mp 170–172° C.; $^1$H NMR (300 MHz, DMSO-d$_6$) δ 7.70–7.20 (m, 8 H), 4.70–4.95 (m, 4 H), 7.25 (brs, 2 H), 3.80–3.20 (m, 12 H).

EXAMPLE 93

1-(2"-Bromo-5"-nitrophenyl)-3-(4'-benzyl-1'-piperazinyl)-1-propanone dihydrochloride: mp 230° C. (dec.); $^1$H NMR (300 MHz, DMSO-d$_6$) δ 8.60 (s, 1 H), 8.25 (d, 1 H), 8.05 (d, 1 H), 7.65–7.40 (m, 5 H), 4.30 (brs, 2 H), 3.80–3.20 (m, 12 H).

EXAMPLE 94

3-(4'-Benzyl-1'-piperazinomethyl)-thiochroman-4-one dihydrochloride: mp >250° C. (dec.); $^1$H NMR (300 MHz, D₂O) δ 7.90 (d, 1 H), 7.37 (m, 6 H), 7.25 (m, 1 H), 7.14 (m, 1 H), 4.32 (s, 2 H), 3.70–3.33 (m, 10 H), 3.24 (m, 2 H), 3.17 (m, 1 H).

EXAMPLE 95

1-(5"-Chloro-4"-nitro-2"-thienyl)-3-(4'-benzyl-1'-piperazinyl)-1-propanone dihydrochloride: To a mixture of isopropanol (25 mL) and concentrated hydrochloric acid (1.45 mL, 0.017 mol) was added 1-benzylpiperazine (1.00 g, 5.68 mmol) to form the hydrochloride salt in situ. Paraformaldehyde (0.34 g, 11.36 mmol) was then added followed by 5-acetyl-2-chloro-3-nitrothiophene (1.28 g, 6.25 mmol). The resulting mixture was refluxed for 72 h. A white solid precipitate formed, was filtered and the filter cake was triturated with methanol to give 0.99 g (44%) of the desired product: mp 220–223° C.; ¹H NMR (300 MHz, D₂O/DMSO-d₆) δ 8.57 (s, 1 H), 7.65–7.45 (m, 5 H), 4.37 (s, 2 H), 7.65–7.45 (m, 5 H), 4.37 (s, 2 H), 3.65–3.30 (m, 12 H).

EXAMPLE 96

1-(2"-Thienyl)-3-(4'-benzyl-1'-piperidinyl)-1-propanone hydrochloride: mp 189–190° C.; ¹H NMR (300 MHz, CDCl₃) δ 12.55–12.35 (brs, 1 H), 7.95 (d, 1 H), 7.73 (d, 1 H), 7.35–7.05 (m, 6 H), 3.73 (t, 2 H), 3.60–3.35 (m, 4 H), 2.75–2.55 (m, 4 H), 2.35–1.95 (m, 2 H), 1.90–1.65 (m, 3 H).

EXAMPLE 97

1-(5"-Bromo-2"-thienyl)-3-(4'-p-fluorobenzoyl-1'-piperidinyl)-1-propanone hydrochloride: mp 201–203° C.; ¹H NMR (300 MHz, DMSO-d₆) δ 10.55–10.33 (brs, 1 H), 8.30–8.20 (m, 2 H), 8.07 (d, 1 H), 7.70–7.50 (m, 3 H), 3.90–3.15 (m, 6 H), 2.25–1.95 (m, 5 H).

EXAMPLE 98

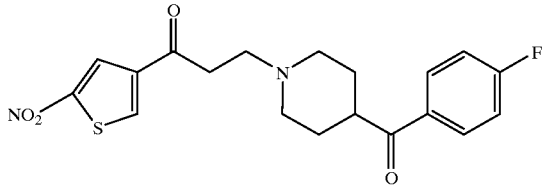

1-(2"-Nitro-4"-thienyl)-3-(4'-p-fluorobenzoyl-1'-piperidinyl)-1-propanone hydrochloride: mp 205–206° C.; ¹H NMR (300 MHz, DMSO-d₆) δ 10.55–10.35 (brs, 1 H), 8.80 (s, 1 H), 8.08 (s, 1 H), 8.10 (dd, 2 H), 7.37 (dd, 2 H), 3.75–3.50 (m, 5 H), 3.50–3.35 (m, 2 H), 3.20–3.00 (m, 2 H), 2.10–1.80 (m, 4 H).

EXAMPLE 99

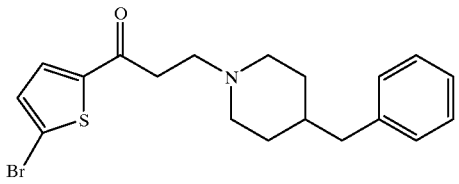

1-(5"-Bromo-2"-thienyl)-3-(4'-benzyl-1'-piperidinyl)-1-propanone hydrochloride: mp 205–208° C.; ¹H NMR (300 MHz, CDCl₃) δ 7.44 (d, 1 H), 7.35–6.95 (m, 6 H), 3.2 (t, 2 H), 2.88 (m, 2 H), 2.77 (t, 2 H), 2.53 (m, 2 H), 1.96 (m, 2 H), 1.74–1.43 (m, 3 H), 1.3 (m, 2 H).

EXAMPLE 100

1-(5"-Bromo-2"-thienyl)-3-(4'-[2'"-chloro-6'"-methylpyrido-4'"-yl]-1'-piperazinyl)-1-propanone dihydrochloride: A mixture of 2-acetyl-5-bromothiophene (0.50 g, 2.44 mmol), the compound from example 49s (0.45 g, 1.88 mmol), paraformaldehyde (73.0 mg, 2.44 mmol), and concentrated hydrochloric acid (0.19 mL, 2.26 mmol) in 20 mL isopropanol were refluxed 72 h. The reaction was cooled and filtered. The mother liquor was concentrated, basified (NaHCO₃) and extracted with CH₂Cl₂. The evaporated residue was purified via flash chromatography (Silica:EtOAc). The resulting oil was dissolved in ether and formed into its corresponding hydrochloride salt by the addition of dry ether/HCl to give 25 mg (2.7%) of the desired product: mp 214–215° C.; ¹H NMR of the free base (300 MHz, CDCl₃) δ 7.46 (d, 1 H), 7.18–6.99 (m, 3 H), 3.75 (brm, 2 H), 3.35 (brm, 2 H), 3.04 (t, 2 H), 2.87 (t, 2 H), 2.70–2.32 (m, 7 H).

EXAMPLE 101

1-(5"-Bromo-2"-thienyl)-3-(4'-benzenesulfonyl-1'-piperazinyl)-1-propanone dihydrochloride: A mixture of 2-acetyl-5-bromothiophene (0.33 g, 1.60 mmol), the compound of example 49r (0.30 g, 1.33 mmol), paraformaldehyde (48.0 mg, 1.60 mmol), and concentrated hydrochloric acid (0.17 mL, 1.99 mmol) in 15 mL isopropanol were refluxed for 16 h. The reaction was cooled, filtered and the filter cake was recrystallized from methanol to give 40 mg (7.4%) of the desired product mp 129–130° C.; ¹H NMR free base (300 MHz, CDCl₃/NaOD) δ 7.74 (m, 2 H), 7.65–7.45 (m, 3 H), 7.40 (m, 1 H), 7.07 (m, 1 H), 2.98 (m, 6 H), 2.8 (m, 2 H), 2.57 (m, 4 H).

EXAMPLE 102

1-(p-Nitrophenyl)-3-(4'-benzenesulfonyl-1'-piperazinyl)-1-propanone dihydrochloride: mp 193–195° C.; ¹H NMR free base (300 MHz, CDCl₃) δ 8.30 (d, 2H), 8.10 (d, 2H), 7.75 (m, 2H), 7.57 (m, 3H), 3.18 (t, 2H), 3.03 (m, 4H), 2.86 (t, 2H), 2.60 (m, 4H).

EXAMPLE 103

1-(p-Nitrophenyl)-3-[4'-(4"-methyl-1",2",3"-thiadiazol-5"-yl)]-1'-piperazinyl)-1-propanone dihydrochloride: mp 207–209° C.; ¹H NMR (300 MHz, D₂O) δ 8.38 (d, 2H), 8.21 (d, 2H), 4.40–3.25 (m, 12H), 2.72 (s,3H).

EXAMPLE 104

1-(4"-Morpholino-3"-nitrophenyl)-3-(4'-benzyl-1'-piperazinyl)-1-propanone trihydrochloride: ¹H NMR (300 MHz, DMSO-d₆) δ 12.25–11.55 (brs, 2H), 9.65–9.45 (brs, 1H), 8.75 (s, 1H), 8.75 (d, 1H), 7.75–7.30 (m, 6H), 4.60–4.20 (brs, 2H), 4.00–3.00(m, 20H).

EXAMPLE 105

1-(3"-Nitro-4"-N-piperidinophenyl)-3-(4'-benzyl-1'-piperazinyl)-1-propanone trihydrochloride: ¹H NMR (300 MHz, DMSO-d₆) δ 11.95–11.70 (brs, 3H), 8.35 (s, 1H), 8.04 (d, 1H), 7.75–7.55 (brs, 2H), 7.55–7.40 (brs, 3H), 7.35 (d, 1H), 4.60–3.00 (m, 18H), 1.80–1.30 (brs, 6H).

EXAMPLE 106

1-(5"-Methyl-2"-thienyl)-3-(4'-benzyl-1'-piperazinyl)-1-propanone dihydrochloride: mp 220° C. (dec.); ¹H NMR (300 MHz, CDCl₃/NaOD) δ 7.53 (m, 1 H), 7.40–7.08 (m, 5 H), 6.78 (m, 1 H), 3.50 (s, 2 H), 3.04 (t, 2 H), 2.83 (t, 2 H), 2 67–2.30 (m, 11 H).

EXAMPLE 107

1-[4"-p-(5'",4'"-Dichloroimidazol-1'"-yl)phenyl]-3-(4'-benzyl-1'-piperazinyl)-1-propanone dihydrochloride: mp 200–202° C.; $^1$H NMR (300 MHz, DMSO-$d_6$) δ 12.25–11.30 (brs, 2 H), 8.30–8.10 (m, 3 H), 7.77 (d, 2 H), 7.70–7.30 (m, 5 H), 4.35 (brs, 2 H), 3.90–3.20 (m, 12 H).

EXAMPLE 108

1-[5"-(Phenylethynyl)-2"-thienyl]-3-(4'-benzyl-1'-piperazinyl)-1-propanone dihydrochloride: mp 205° C. (dec.); $^1$H NMR (300 MHz, DMSO-$d_6$) δ 12.30–11.20 (brs, 2 H), 8.00 (d, 1 H), 7.80–7.30 (m, 11 H), 4.30 (brs, 2 H), 3.90–3.00 (m, 12 H).

EXAMPLE 109

1-(3"-Nitrophenyl)-3-(4'-piperonyl-1'-piperazinyl)-1-propanone dihydrochloride: mp 215° C. (dec.); $^1$H NMR (300 MHz, DMSO-$d_6$) δ 12.35–11.20 (brs, 2 H), 8.70 (s, 1 H), 8.52 (d, 1 H), 8.40 (d, 1 H), 7.70 (dd, 1 H), 7.25 (s, I H), 7.15–6.90 (m, 2 H), 6.05 (s, 1 H), 4.25 (brs, 2 H), 3.90–3.10 (m, 12 H).

EXAMPLE 110

1-(5"-Methyl-3"-phenylisoxazol-4"-yl)-3-(4'-benzyl-1'-piperazinyl)-1-propanone dihydrochloride: mp 220° C. (dec.); $^1$H NMR (300 MHz, DMSO-$d_6$) δ 12.35–11.40 (brs, 2 H), 7.70–7.30 (m, 10 H), 4.35 (brs, 2 H), 3.70–3.10 (m, 12 H), 2.80 (s, 3 H).

EXAMPLE 111

1-(2"-Phenylthiazol-4"-yl)-3-(4'-benzyl-1'-piperazinyl)-1-propanone dihydrochloride: mp 220° C. (dec.); $^1$H NMR (300 MHz, DMSO-$d_6$) δ 12.20–11.50 (brs, 2 H), 8.65 (s, I H), 8.10–7.90 (brs, 2.H), 7.75–7.30 (m, 8 H), 4.30 (brs, 2 H), 3.80–3.20 (m, 12 H).

EXAMPLE 112

1-(3"-Phenylisoxazol-4"-yl)-3-(4'-benzyl-1'-piperazinyl)-1-propanone dihydrochloride: mp 212° C. (dec.); $^1$H NMR (300 MHz, DMSO-$d_6$) δ 12.25–11.40 (brs, 2 H), 8.10–7.90 (m, 3.H), 7.70–7.30 (m, 8 H), 4.35 (brs, 2 H), 3.80–3.10 (m, 12 H).

EXAMPLE 113

1-(4"-[2'",4'"-Dinitrophenylamino]phenyl)-3-(4'-benzyl-1'-piperazinyl)-1-propanone dihydrochloride: mp 248–250° C.; $^1$H NMR (300 MHz, CDCl$_3$/NaOD) δ 9.20 (m, 1 H), 8.26 (m, 1 H), 8.08 (m, 2 H), 7.50–7.10 (m, 8 H), 3.53 (s, 2 H), 3.21 (m, 2 H), 2.87 (m, 2 H), 2.55 (brm, 8 H).

EXAMPLE 114

1-(2",4"-Dimethylthiazol-5"-yl)-3-(4'-benzyl-1'-piperazinyl)-1-propanone dihydrochloride: mp: 228° C. (dec); $^1$H NMR (300 MHz, D$_2$O) δ 7.55 (brs, 5 H), 4.50 (s, 2 H), 3.87–3.42 (m, 12 H), 2.75 (s, 3 H), 2.67 (s, 3 H).

EXAMPLE 115

1-(m-Nitrophenyl)-3-(4'-benzyl-1'-piperidinyl)-1-propanone hydrochloride: mp 189–191° C.; $^1$H NMR (300 MHz, CDCl$_3$) δ 12.60–12.40 (brs, 1 H), 8.35 (d, 2 H), 8.18 (d, 2 H), 7.35–7.05 (m, 5 H), 3.95 (t, 2 H), 3.65–3.35 (m, 4 H), 2.80–2.55 (m, 4 H), 2.20–1.65 (m, 5 H).

EXAMPLE 116

The following compounds may be prepared by the general method:

(a) 1-(6"-Bromocoumarin-3"-yl)-3-(4'-benzyl-1'-piperazinyl)-1-propanone dihydrochloride

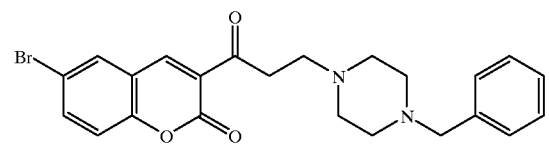

(b) 1-(6"-Bromocoumarin-3"-yl)-3-(4'-benzoyl-1'-piperazinyl)-1-propanone dihydrochloride (c) 1-(1",1"-Dimethyl-6"-tert-butylindan-4"-yl)-3-(4'-benzyl-1'-piperazinyl)-1-propanone dihydrochloride (d) 1-(1",1"-Dimethyl-6"-tert-butylindan-4"-yl)-3-(4'-benzoyl-1'-piperazinyl)-1-propanone dihydrochloride (e) 1-(Coumarin-3"-yl)-3-(4'-benzyl-1'-piperazinyl)-1-propanone dihydrochloride (f) 1-(Coumarin-3"-yl)-3-(4'-benzoyl-1'-piperazinyl)-1-propanone dihydrochloride (g) 1-(5"-Cyano-4"-methyl-2"-(methylthio)thien-3"-yl)-3-(4'-benzyl-1'-piperazinyl)-1-propanone dihydrochloride (h) 1-(5"-Cyano-4"-methyl-2"-(methylthio)thien-3"-yl)-3-(4'-benzoyl-1'-piperazinyl)-1-propanone dihydrochloride (i) 1-(p-(2",4"-Dichlorophenoxy)-phenyl)-3-(4'-benzyl-1'-piperazinyl)-1-propanone dihydrochloride (j) 1-(p-(2",4"-Dichlorophenoxy)-phenyl)-3-(4'-benzoyl-1'-piperazinyl)-1-propanone dihydrochloride (k) 1-(5'"-(2",4"-Difluorophenoxy)-fur-2'"-yl)-3-(4'-benzyl-1'-piperazinyl)-1-propanone dihydrochloride

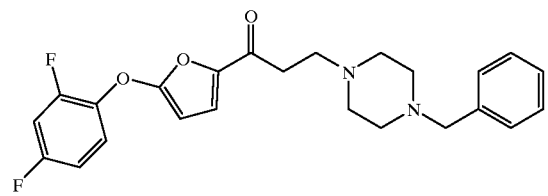

(l) 1-(5'"-(2",4"-Difluorophenoxy)-fur-2'"-yl)-3-(4'-benzoyl-1'-piperazinyl)-1-propanone dihydrochloride (m) 1-(2",3"-Dihydrobenzo[b]fur-5"-yl)-3-(4'-benzyl-1'-piperazinyl)-1-propanone dihydrochloride

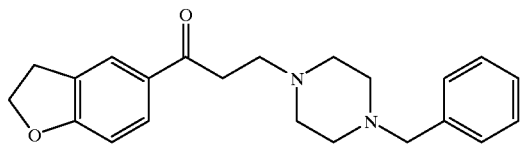

(n) 1-(2",3"-Dihydrobenzo[b]fur-5"-yl)-3-(4'-benzoyl-1'-piperazinyl)-1-propanone dihydrochloride (o) 1-(3",5"-Dimethylbenzo[b]thien-2"-yl)-3-(4'-benzyl-1'-piperazinyl)-1-propanone dihydrochloride (p) 1-(3",5"-Dimethylbenzo[b]thien-2"-yl)-3-(4'-benzoyl-1'-piperazinyl)-1-propanone dihydrochloride

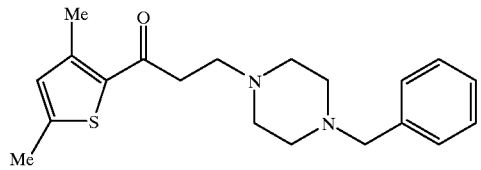

(q) 1-(2",4"-Dimethylthien-5"-yl)-3-(4'-benzyl-1'-piperazinyl)-1-propanone dihydrochloride (r) 1-(2",4"-Dimethylthien-5"-yl)-3-(4'-benzoyl-1'-piperazinyl)-1-propanone dihydrochloride (s) 1-(p-[Phenylthio]phenyl)-3-(4'-benzyl-1'-piperazinyl)-1-propanone dihydrochloride (t) 1-(p-[Phenylthio]phenyl)-3-(4'-benzoyl-1'-piperazinyl)-1-propanone dihydrochloride (u) 1-(3"-Methoxycarbonyl-5"-methylisoxazol-4"-yl)-3-(4'-benzyl-1'-piperazinyl)-1-propanone dihydrochloride (v) 1-(3"-Methoxycarbonyl-5"-methylisoxazol-4"-yl)-3-(4'-benzoyl-1'-piperazinyl)-1-propanone dihydrochloride (w) 1-(5"-(2'"-Carbomethoxythien-3'"-yl)-furan-2"-yl)-3-(4'-benzyl-1'-piperazinyl)-1-propanone dihydrochloride (x) 1-(5"-(2'"-Carbomethoxythien-3'"-yl)-furan-2"-yl)-3-(4'-benzoyl-1'-piperazinyl)-1-propanone dihydrochloride (y) 1-(p-(4"-Methoxyphenoxy)-phenyl)-3-(4'-benzyl-1'-piperazinyl)-1-propanone dihydrochloride (z) 1-(p-(4"-Methoxyphenoxy)-phenyl)-3-(4'-benzoyl-1'-piperazinyl)-1-propanone dihydrochloride (aa) 1-(p-(4"-Nitrophenoxy)-phenyl)-3-(4'-benzyl-1'-piperazinyl)-1-propanone dihydrochloride (bb) 1-(p-(4"-Nitrophenoxy)-phenyl)-3-(4'-benzoyl-1'-piperazinyl)-1-propanone dihydrochioride (cc) 1-(m-Nitro-p-(phenylthio)-phenyl)-3-(4'-benzyl-1'-piperazinyl)-1-propanone dihydrochloride

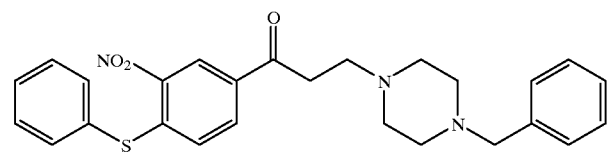

(dd) 1-(m-Nitro-p-(phenylthio)-phenyl)-3-(4'-benzoyl-1'-piperazinyl)-1-propanone dihydrochloride (ee) 1-(m-Nitro-p-(1"-piperidinyl)-pheny)-3-(4'-benzoyl-1'-piperazinyl)-1-propanone dihydrochloride (ff) 1-(m-Nitro-p-(4"-morpholino)-phenyl)-3-(4'-benzoyl-1'-piperazinyl)-1-propanone dihydrochloride (gg) 1-(p-Nitrophenyl)-3-(4'-(5"-(1'"-methyl-3'"-triuoromethylpyrazol-5'"-yl)-thien-2"yl)-1'-piperazinyl)-1-propanone

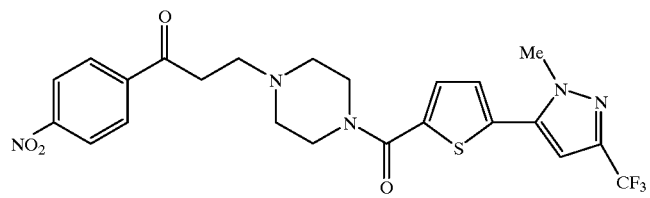

dihydrochloride (hh) 1-(5"Bromo-2"-thienyl)-3-(4'-p-bromobenzenesulfonyl-1'-piperazinyl)-1-propanone hydrochloride.

(ii) 1-(5"Bromo-2"-thienyl)-3-(4'-p-toluenesulfonyl-1'-piperazinyl)-1-propanone hydrochloride.

(jj) 1-(p-Nitrophenyl)-3-(4'-p-bromobenzenesulfonyl-1'-piperazinyl)-1-propanone hydrochloride.

(jj) 1-(5"-Chloro-4"-nitro-2"-thienyl)-3-(4'-benzenesulfonyl-1'-piperazinyl)-1-propanone hydrochloride.

(kk) 1-(2"-Chloro-3"-nitrothien-5"-yl)-3-(4'-o-trifluoromethylbenzoyl-1'-piperazinyl)-1-propanone dihydrochloride.

(ll) 1-(p-Nitrophenyl)-3-(4'-[4"-methyl-1",2",3"-thiadiaz-5"-oyl]-1'-piperazinyl)-1-propanone dihydrochloride.

(mm) 1-(5"-Chloro-4"-nitro-2"-thienyl)-3-[4'-(4'"-methyl-1'",2'",3'"-thiadiaz-5'"-oyl)-1'-piperazinyl]-1-propanone dihydrochloride.

(nn) 1-[5"-Cyano-4"-methyl-2"-(methylthio)-3"-thienyl]-3-(4'-benzyl-1'-piperazinyl)-1-propanone dihydrochloride.

(oo) 1-(2",4"-Dimethyl-5"-thiazolyl)-3-(4'-benzyl-1'-piperazinyl)-1-propanone dihydrochloride.

(pp) 1-(5"-Nitro-3"-thienyl)-3-(4'-o-fluorobenzoyl-1'-piperazinyl)-1-propanone dihydrocholoride.

(qq) 1-(5"-Bromo-2"-thienyl)-3-(4'-o-fluorobenzoyl-1'-piperazinyl)-1-propanone dihydrocholoride.

EXAMPLE 117

Effect of Chlorpromazine on Paired Helical Filament Levels in Human Brain Tissue The in vitro analyses described herein to investigate the activity of the compounds of this invention can also be used to determine the nature of abnormally phosphorylated paired helical filament epitopes involved in Alzheimer's Disease, the regulatory mechanisms involved with Alzheimer's Disease and modifications of the protein tau and other polypeptides associated with PHFs and involved in Alzheimer's Disease.

Figure 3:
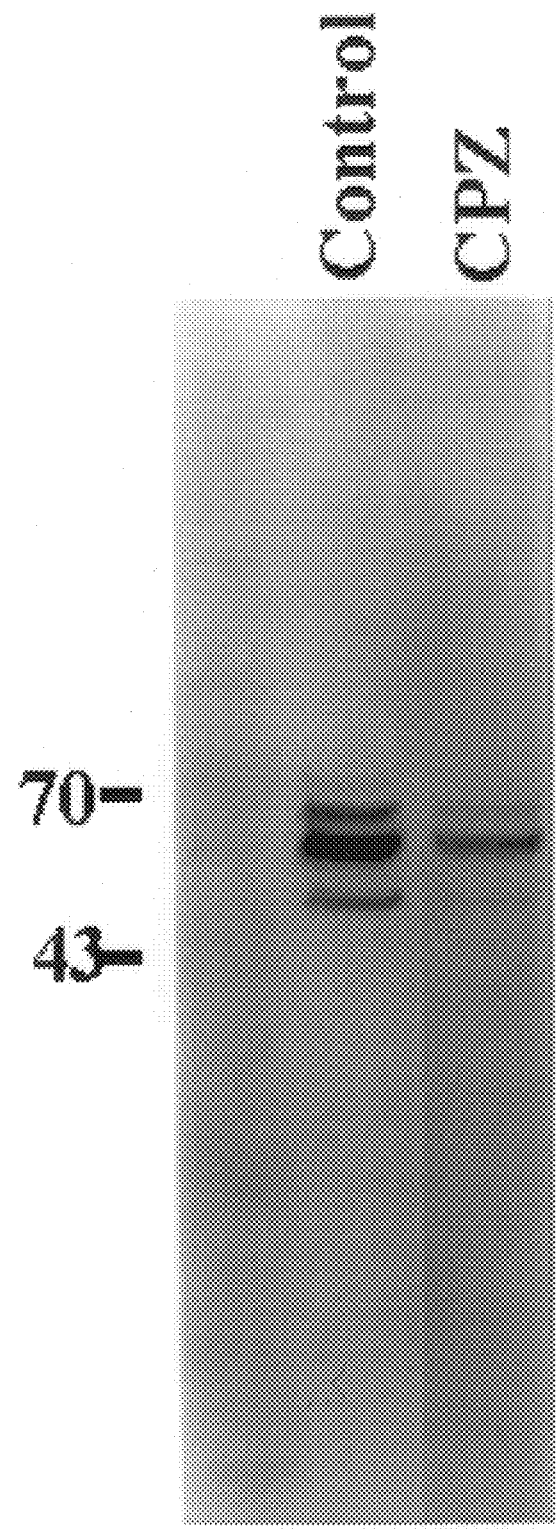
FIG. 3 is a western blot showing PHF-1 immunoreactivity in lysates from control and chlorpromazine treated MSN cells treated with okadaic acid.

Certain phenothiazines, for example, chlorpromazine, can markedly inhibit the expression of PHF epitopes (as determined by loss of immunoreactivity with Alzheimer's Disease specific antibodies) upon treatment of MSN1a cells with okadaic acid (cf. FIG. 3). These compounds are effective at micromolar concentrations, with increased potency being evident when cells are treated prior to the addition of okadaic acid. The effective concentrations appear to be in the range at which these drugs are present in the brain following chronic treatment of psychiatric patients (Svendsen, C N, Psychopharrnacology, 90, 316–321, 1986). These results indicate that patients who were chronically treated with phenothiazines would be protected from the development of PHF, and thus would have a low probability of development of Alzheimer's Disease.

Frontal and cortical brain tissue specimens obtained at autopsy from patients chronically treated with chlorpromazine were analyzed using the ALZ-EIA method previously described (Ghanbari, H A, et al, JAMA, 263, 2907, 1990). The results are shown in FIGS. 4A and 4B frontal (Broadman area 10) and temporal (Broadman area 38) regions, respectively. The brain tissue (post-mortem) from approximately the same number of (age matched) normal controls and Alzheimer's Disease patients were also analyzed and are presented in these figures as negative and positive controls (for normal and AD, respectively). As the data indicate, the samples from chlorpromazine treated patients (Rx) had low PHF epitope levels similar to normal controls, whereas the PHF epitope levels in the AD group were clearly much higher. Furthermore, these results were consistent with histopathological diagnosis of the brain specimens. Statistically, in the general population, about 20–30% of the individuals in the Rx age group would have developed AD and hence much higher PHF in the brain regions indicated (Katzman, R., Kawas, C. H., pages 105–122, in Alzheimer's Disease, Eds., Terry, R D; Katzman, R; Bick, K L. Raven Press, New York, 1994). This evidence shows that chronic treatment of patients with chlorpromazine prevents PHF formation and AD.

In a subsequent study, 51 additional patients were identified and the analysis was repeated as above using the TG3 antibody in an ELISA format. The results, summarized in Table 1, clearly reproduce and confirm the first retrospective study. Immunohistopathological studies carried out on several brain regions from these patients were consistent with these ELISA results. Taken together, these two studies provide evidence of the therapeutic benefit of chlorpromazine in AD and validate the use of the MSN1a model for the identification of therapeutically usefull compounds for the treatment of AD.

TABLE 1

|  | N | MEAN AGE ± SEM | SIGNAL* ± SEM | |
| --- | --- | --- | --- | --- |
|  |  |  | Frontal | Temporal |
| Normal | (12) | 79.50 ± 3.33 | 0.12 ± 0.12 | 0.00 ± 0.00 |
| AD | (28) | 82.54 ± 1.94 | 16.54 ± 2.59 | 17.55 ± 2.82 |
| Rx | (51) | 76.88 ± 1.55 | 0.12 ± 0.11 | 0.16 ± 0.11 |

*Signal is calculated by summing the means of duplicate absorbance readings (direct ELISA using TG3 antibody) for 8 dilutions of all lysates prepared by one to two serial dilutions.

Efforts to dissect the characteristic lesions of Alzheimer's Disease, namely the neurofibrillary tangles and the neuritic plaques have indicted that aberrant protein phosphorylation is a hallmark of the cytoskeletal abnormalities in AD. Phosphorylated sites on the PHFs found in neurofibrillary tangles and abnormal neurites are detected by AD-specific antibodies, such as TG3 and PHF-1, in the brains of AD patients and not in normal or other neurodegenerative disease controls (cf. FIGS. 1, 2A). In the MSN Ia cell culture model (cf. FIGS. 2B, 3), these aberrantly phosphorylated PHF sites are also detected by these antibodies.

Figure 2B:
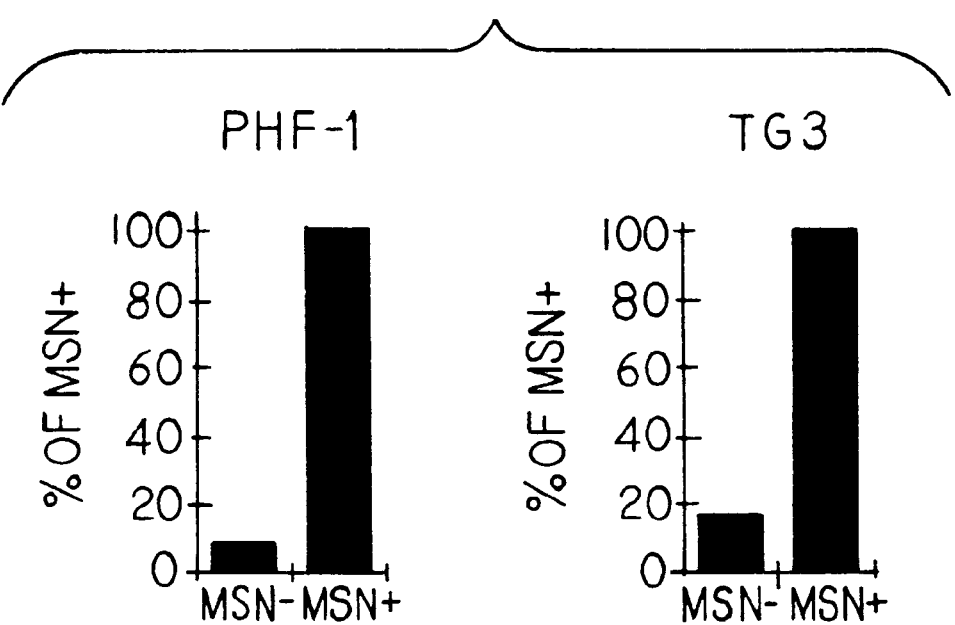
FIG. 2B is a graphic comparison of MSN1a cell lysate (minus or plus okadaic acid) immunoreactivity toward PHF-1 and TG3 antibodies expressed as a percent of total immuonreactivity in lysates of MSN+ okadaic acid.

Therefore, the therapeutic activity of the compounds of the invention was assessed by the ability of these agents to affect the production of abnormally phosphorylated epitopes pertinent to the production of PHFs of AD, utilizing a human neuroblastoma cell line (MSN1a) in the presence of the protein phosphatase inibitor, okadaic acid (OKA). As described above, chlorpromazine, a clinically used antipyschotic, prevents production of the aberrantly phosphorylated PHF epitopes and, hence, the production of PHFs, thereby preventing AD. As shown in FIGS. 2B and 3 and in Table 2, chlorpromazine is effective in inhibiting the production of these aberrant phosphorylated epitopes in the MSN1a cell culture model as determined by the prevention of the immunoreactivity associated with PHF antibodies such as TG3 which was utilized in the retrospective clinical analysis.

To determine the effect of chlorpromazine on the paired helical filament epitopes associated with AD, MSN1a cells expressing paired helical filament epitopes were incubated with 100 mM chlorpromazine (CPZ) or a 0.2% DMSO vehicle control for 2 hours at 37° C. The cells were isolated by centrifugation, boiled for 10 minutes and 25 mg protein from the resulting heat stable supernatants were loaded per lane on an SDS-PAGE gel. The gel was electrophoretically transferred to nitrocellulose membrane and then immunostained with PHF-1. As shown in FIG. 3, CPZ greatly decreased the production of paired helical filament epitopes by the MSN1a cells. In contrast, the control shows that without the addition of CPZ, there was production of paired helical filament epitopes by the MSN1a cells. The use of the MSNIa cell culture model for screening of novel compounds for therapeutic activity in AD is, therefore, quite warranted.

This assay can thus be used to determine whether a drug is capable of preventing or intervening in AD by attenuating the production of abnormally phosphorylated paired helical filament epitopes associated with AD. To determine whether a drug is capable of preventing or intervening in AD activity, the MSN1a cells containing tau and associated proteins are treated with OKA capable of greatly increasing immunoreactivity of the MSN1a cells with AD specific monoclonal antibodies. Then, either prior to or concomitantly with OKA treatment, a compound of the present invention is added to the culture. If the compound prevents the induction of the AD epitopes in the MSN1a cells treated with OKA, then it is said to have anti-AD activity. If the AD-specific antibodies are highly reactive with the neuroblastoma cells following OKA treatment in the presence of compound, then the compound is said to be ineffectual against AD.

The MSN1a human neuroblastoma line was subcloned from a population of MSN cells obtained from the laboratory of Dr. Peter Davies (Albert Einstein College of Medicine, New York, N.Y.). Cells were grown and maintained in flasks in RPMI 1640 medium, supplemented with 15% fetal calf serum, 100 U/ml penicillin, 100 U/ml Streptomycin, 0.5 ug/ml fungizone under 7.5% $CO_2$ at 37° C.

Stock solutions of drugs were prepared by dissolving the anhydrous powders to final concentrations of either 10 or 20 mM in 50% aqueous or 100% dimethyl sulfoxide (DMSO), respectively. Working solutions of drugs were prepared by dilution of the stock solutions with Kreb's Ringer in Hepes buffer (KRH) (128 mM NaCl, 5 mM KCl, 2.5 mM $CaCl_2$ 1.2 mM $MgSO_4$, 1 mM $Na_2HPO_4$, 10 mM dextrose, 20 mM Hepes, pH 7.4). OKA is maintained as a 1 mM stock solution in DMSO prior to dilution to 4 $\mu$M in KRH.

MSN cells grown in 225 $cm^2$ flasks are removed from the incubator, their medium decanted and replaced with 50 ml pre-warmed KRH. The cells are harvested by scraping prior to sedimentation at 1000 rpm for 5 min. The supernatants are discarded and the cell pellets are resuspended, the cells counted and diluted to a density of $2\times10^4$ cells/50 ml. The cells are then plated in a 96 well plate at 50 $\mu$l/well and 25 $\mu$l of 4 $\mu$M OKA and 25 $\mu$l of drug are then added to the appropriate wells; the entire 96 well plate is then incubated for 2 hrs at 37° C. Depending on the dilution of drug added, this yields individual wells containing 1 $\mu$M OKA, 0–64 $\mu$M drug and 2>$10^4$ cells in 0.26% DMSO in KRH. The incubation is terminated by the addition of 20 $\mu$l of 6× extraction buffer and immediate freezing at −80° C. for at least one hr. The 6× extraction buffer contains: 25 mM Tris-HCl, pH 7.6, 150 mM NaCl, 5 mM EDTA, 24 mM β-glycerol phosphate, 10 $\mu$g/ml APMSF (4-amidinophenylmethane-sulfonyl flouride), and 2.5 $\mu$g/ml each of leupeptin, aprotinin, and pepstatin. The plates are thawed in a 37° C. water bath and 20 $\mu$l of cell lysate is added to a replica well in an ELISA plate that already contains 80 1 of coating buffer (15 mM $Na_2CO_3$ and 35 mM $NaHCO_3$, pH 9.6). The plates are allowed to coat overnight at 4° C. The plates are washed four times with deionized water and then blocked for 30 min at 37° C. with 200 $\mu$l/well pre-warmed 1% bovine serum albumin in 10 mM Tris-HCl, pH 7.4, 150 mM NaCl, 3 mM $NaN_3$ (BSA-TBS). After the blocking solution is removed, 100 $\mu$l/well of an appropriate dilution of pre-warmed primary antibody (eg., TG3 or PHF-1) in BSA-TBS is added and incubated at 37° C. for 30 min. Incubation is terminated by washing four times in deionized water at which time 100 $\mu$l of an appropriate dilution of pre-warmed secondary antibody (conjugated to alkaline phosphatase) in BSA-TBS is added to each well in the ELISA plate. Incubation is performed for 30 min at 37° C. followed by washing 4 times with deionized water. 100 $\mu$l/ml of prewarmed chromogenic substrate (1 mg/ml p-nitrophenyl phosphate in 10% diethanolamine, 3 mM $NaN_3$, 0.5 mM $MgCl_2$, pH 9.8) is added and the plate incubated for 30 min at 37° C. Absorbance at 405 nm is then determined by reading the plate on a BioRad UV Microplate Reader.

Results obtained from the MSN1a cell culture model studies utilizing the TG3 antibody are shown in Table 2.

TABLE 2

IC50 for inhibition of TG3 immunoreactivity in OKA treated MSN1a cells

| Example # | IC50 ($\mu$M) |
| --- | --- |
| Chlorpromazine | ~70.0 |
| 5 | 5.0 |
| 10 | 6.0 |
| 11 | 4.2 |
| 13 | 11.0 |
| 14 | 5.8 |
| 16 | 5.2 |
| 19 | 15.6 |
| 21 | 6.6 |
| 26 | 14.7 |
| 29 | 8.7 |
| 32 | 6.2 |
| 36 | 25.0 |
| 39 | 10.0 |
| 42 | 5.7 |
| 44 | 7.5 |
| 55 | 6.3 |
| 57 | 6.8 |
| 63 | 7.3 |
| 67 | 20.0 |
| 69 | 15.0 |
| 76 | 10.5 |

TABLE 2-continued

IC50 for inhibition of TG3 immunoreactivity in
OKA treated MSN1a cells

| Example # | IC50 ($\mu$M) |
|---|---|
| 80 | 5.7 |
| 81 | 4.5 |
| 91 | 9.5 |
| 95 | 2.8 |
| 98 | 34 |

As seen in Table 2, the compounds of the present invention are potent inhibitors of the production of the aberrantly phosphorylated epitopes as detected in the MSN1a cell culture model system utilizing the antibody TG3. As shown, the compounds of the present invention are more potent than chlorpromazine, a compound shown to inhibit the production of the AD associated epitopes and to prevent AD. The compounds of the present invention are thus useful in the treatment of AD.

EXAMPLE 118

Determination of Antineoplastic Activity

The compounds of the invention according to formula I are effective in destabilizing microtubules, thus are useful in treating certain neoplastic diseases. Indirect immunofluorescence microscopy using the monoclonal antibodies to tubulin is used herein to determine the activity of the compounds of this invention in promoting depolymerization of the microtubule cytoskeleton in cultured cells. The following assay was employed.

Cultured human CG neuroblastoma cells were seeded 1:3 from confluent cultures onto sterile 11×22 mm coverslips in 6 well tissue culture plates 16 hr prior to treatment. The following day, the tissue culture medium is removed and the cells are exposed to various concentrations of compounds of this invention in Krebs Ringer Hepes (KRH) buffer containing a final concentration of 0.5% DMSO as carrier. Incubations were performed at 37° C. in a humidified 5% $CO_2$ atmosphere for 2 hr. After incubation, the cells were fixed in 3% TEM grade formaldehyde in PBS for 45 min at room temperature.

To visualize the effects of the compounds of the invention on the microtubule cytoskeleton, the cells were processed for tubulin immunofluorescence. Briefly, the cells were permeabilized in 0.5% Triton-X 100 in PBS for 5 min. The cells were washed 2x with PBS and aldehydes reduced using 0.5 mg/ml $NaBH_4$ in PBS for 5 min. Subsequently, the cells were blocked for 10 min in 1.5% BSA and 1.5% nonfat dry milk in PBS (blocking solution, BS) for 10 min. The cells were then incubated for 30 min at 37° C. with the monoclonal antibody Tu27B which recognizes b-tubulin (dilution 1:20 in BS). Subsequently, the cells were washed 2x in PBS and once in BS. The cells were then incubated for 30 min at 37° C. with sheep antimouse IgG conjugated to FITC. After incubation, the cells were washed 2x in PBS and once in BS and incubated for 30 min at 37° C. with rabbit antisheep IgG conjugated to FITC. The cells were rinsed in PBS, counterstained with Hoechst 33285 in PBS (1 $\mu$g/ml), and rinsed in PBS. The coverslips were mounted in 9:1 glycerol:PBS containing 1 mg/ml p-phenylenediamine and sealed with nail polish.

The cells were viewed using a Jenalumar epifluorescence microscope equipped with the proper filters for Fluorescein Isothiocyanate (FITC) excitation and emission. Lack of effect of a compound is evidenced by the presence of an intact microtubule network in interphase cells, or a mitotic spindle in dividng cells. Antieoplastic compounds of the invention at effective doses result in the disappearance of microtubules in both interphase and mitotic cells.

The results of screening of compounds of the invention are shown in Table 3. Shown for comparative purposes is vinblastine ("Velban", Lilly Research Laboratories), a clinically useful antineoplastic agent which promotes microtubule destabilization, hence microtubule disassembly.

TABLE 3

Antimicrotubule Activity

| Example # | Concentration* ($\mu$M) |
|---|---|
| 5 | 4 |
| 7 | 20 |
| 9 | 20 |
| 10 | 20 |
| 20 | 20 |
| 21 | 20 |
| 22 | 20 |
| 27 | 20 |
| 38 | 20 |
| 40 | 20 |
| 41 | 20 |
| 50 | 20 |
| 60 | 20 |
| 70 | 20 |
| 95 | 20 |
| 85 | 20 |
| 112 | 20 |
| 113 | 20 |
| vinblastine | 0.05 |

*a concentration where microtubule destabilization occurs

As shown in Table 3, the compounds of the present invention promote microtubule destabilization and thus are useful in the treatment of neoplastic diseases.

EXAMPLE 119

Antibacterial Activity Assay

The compounds of the present invention are also effective antibacterial and antifungal agents.

The activity of the compounds is determined using the following assay. The compound is dissolved in DMSO at a concentration of 6 mg/ml and then diluted with water to a final concentration of 3 mg/ml in 50% DMSO (% DMSO was shown not to be inhibitory to the test organisms). An aliquot (0.08 ml) of each drug solution was transferred to filter paper discs (12.7 mm diameter, Scmeicherand Schuell) for use in the agar diffusion assay. The concentration of each drug on the filter paper disc was 240 ug/disc. The test organisms included the following: Gram-positive aerobes (*Staphylococcus aureus* SRI 1323, *Streptococcus pneumoniae* SRI 1167); Gram-negative aerobe (*Proteus vulgaris* SRI 180); and the yeast *Candida albicans* SRI 523. An agar disc diffusion assay was used to evaluate the antimicrobial activity of the test compounds. Briefly, cultures were prepared from 16–20 hr agar slant cultures by inoculating in physiological saline to a turbidity equivalent to a #0.5

McFarland turbidity standard for the bacteria and a #3 McFarland standard for *C. albicans*. The surface of Mueller-Hinton agar (15×100 mm plates, mm) were evenly inoculated with each standardized culture using a cotton swab. Filter paper discs containing the drug concentration listed above were then placed on the inoculated agar plates along with a disc containing the solvent used to dissolve each drug. The plates were incubated at 37° C. for about 24 hr and the diameters of the zones of inhibition measured with a vernier caliper. Positive control drugs consisted of streptomycin for use with the bacterial strains and 5-fluorocytosine for use with *C. albicans*. The positive control drugs were assayed as described above for the compounds of the present invention using the same concentration. Results of screeing a representative sample of the compounds of the present invention are shown in Table 4.

TABLE 4

Antimicrobial and fungicidal activity

| | Diameter of the zone of inhibition (mm) | | | |
|---|---|---|---|---|
| Example # | P. vulgaris | S. pneumoniae | S. aureus | C. albicans |
| 5 | 17.3 | 29.9 | 22.8 | 17.6 |
| 21 | 0[1] | 40.7 | 33.8 | 26.6 |
| 25 | 16.0 | 36.3 | 27.5 | 26.0 |
| 43 | 15.9 | 25.3 | 17.7 | 22.5 |
| 76 | 20.5 | 35.5 | 19.3 | 20.9 |
| 78 | 14.5 | 19.7 | 16.2 | 15.2 |
| 80 | 13.8 | +[2] | 17.2 | 14.5 |
| 86 | 13.9 | 19.3 | 16.2 | 17.3 |
| streptomycin | 37.6 | 39.8 | 28.4 | ND[3] |
| 5-fluoro-cytosine | ND | ND | ND | 33.5 |

[1]no measurable zone of inhibition around the disc.
[2]zone of inhibition too large to measure.
[3]not determined.

As is shown in Table 4, the compounds of the present invention inhibit growth and proliferation of Gram positive and Gram-negative organisms to a degree similar to that demonstrated by the known therapeutically useful agent streptomycin. These compounds also inhibit growth and proliferation of *C. albicans* to a degree similar to that demonstrated by the therapeutically useful 5-fluorocytosine. Therefore, the compounds are therapeutically useful antibacterial and/or antifungal agents.

The foregoing is merely illustrative of the invention and is not intended to limit the invention to the disclosed compounds. From the foregoing, it will be appreciated that although specific embodiments of the invention have been described herein for purposes of illustration, various modifications may be made without deviating from the spirit or scope of the invention.

What is claimed is:

1. A method of inhibiting the formation of abnormally phosphorylated paired helical filament epitopes associated with Alzheimer's Disease comprising administering to a patient susceptible to the disease an amount of a compound effective to inhibit the formation of the abnormally phosphorylated epitopes, where the compound has the formula:

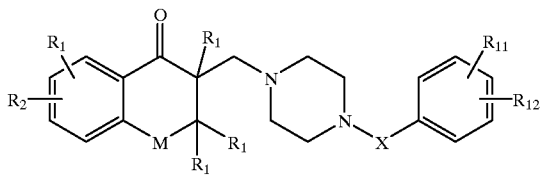

wherein $R_1$ and $R_2$ independently represent hydrogen, phenyl, halogen, nitro, lower alkyl, trifluoroalkyl, lower alkoxy, thioloweralkoxy, cyclohexyl, amino, acetyl, morpholino, cyano, piperidinyl, trifluoroalkoxy, with the proviso that not all of $R_1$ and $R_2$ are hydrogen;

M is oxygen, methylene, or sulfur;

X is methylene or carbonyl; and $R_{11}$ and $R_{12}$ independently represent hydrogen, halogen, trifluoromethyl, nitro, cyano, lower alkyl, lower alkoxy, thioloweralkoxy, and acetyl.

* * * * *